United States Patent
Yi et al.

(10) Patent No.: US 9,743,901 B2
(45) Date of Patent: Aug. 29, 2017

(54) X-RAY IMAGING APPARATUS AND METHOD OF CONTROLLING THE SAME

(71) Applicant: SAMSUNG ELECTRONICS CO., LTD., Suwon-si (KR)

(72) Inventors: Jae Mock Yi, Hwaseong-si (KR); Dong Goo Kang, Hwaseong-si (KR); Young Hun Sung, Hwaseong-si (KR); Jae Hak Lee, Yongin-si (KR); Seok Min Han, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 220 days.

(21) Appl. No.: 14/547,626

(22) Filed: Nov. 19, 2014

(65) Prior Publication Data
US 2015/0139395 A1 May 21, 2015

(30) Foreign Application Priority Data
Nov. 19, 2013 (KR) .................. 10-2013-0140963

(51) Int. Cl.
*A61B 6/00* (2006.01)
*G01N 23/04* (2006.01)
*A61B 6/12* (2006.01)

(52) U.S. Cl.
CPC .......... *A61B 6/542* (2013.01); *A61B 6/4035* (2013.01); *A61B 6/469* (2013.01); *A61B 6/487* (2013.01); *A61B 6/54* (2013.01); *G01N 23/04* (2013.01); *A61B 6/12* (2013.01); *A61B 6/467* (2013.01); *A61B 6/481* (2013.01); *A61B 6/504* (2013.01); *G01N 2223/314* (2013.01); *G01N 2223/427* (2013.01)

(58) Field of Classification Search
CPC ............................... A61B 6/06; A61B 6/469
See application file for complete search history.

(56) References Cited

U.S. PATENT DOCUMENTS

| 5,677,943 A | 10/1997 | Hoebel |
| 2003/0223547 A1 | 12/2003 | Galish et al. |
| 2010/0091937 A1* | 4/2010 | Raupach ............... A61B 6/032 378/16 |
| 2010/0104167 A1 | 4/2010 | Sakaguchi et al. |

(Continued)

FOREIGN PATENT DOCUMENTS

| JP | 6-154198 A | 6/1994 |
| JP | 2013-52232 A | 3/2013 |

(Continued)

OTHER PUBLICATIONS

Communication dated Mar. 19, 2015 issued by the European Patent Office in counterpart European Patent Application No. 14193811.8.

*Primary Examiner* — Dani Fox
(74) *Attorney, Agent, or Firm* — Sughrue Mion, PLLC

(57) ABSTRACT

An X-ray imaging apparatus and method are provided. The X-ray imaging apparatus according to an aspect includes an X-ray source configured to radiate X-rays onto a subject region, an X-ray detector configured to detect the radiated X-rays and obtain a plurality of frame images of the subject region, and an ROI filter located between the X-ray source and the X-ray detector, configured to move toward the X-ray source and the X-ray detector, and configured to filter the X-rays radiated from the X-ray source.

20 Claims, 30 Drawing Sheets

(56) References Cited

U.S. PATENT DOCUMENTS

| | | | | |
|---|---|---|---|---|
| 2012/0057674 | A1* | 3/2012 | Zhang | A61B 5/7285 378/62 |
| 2015/0078516 | A1* | 3/2015 | Ohashi | A61B 6/06 378/42 |
| 2015/0131781 | A1* | 5/2015 | Ohashi | A61B 6/542 378/62 |
| 2015/0272520 | A1* | 10/2015 | Kobayashi | A61B 6/06 378/62 |

FOREIGN PATENT DOCUMENTS

| | | |
|---|---|---|
| KR | 10-2008-0005747 A | 1/2008 |
| KR | 10-2009-0127100 A | 12/2009 |

* cited by examiner

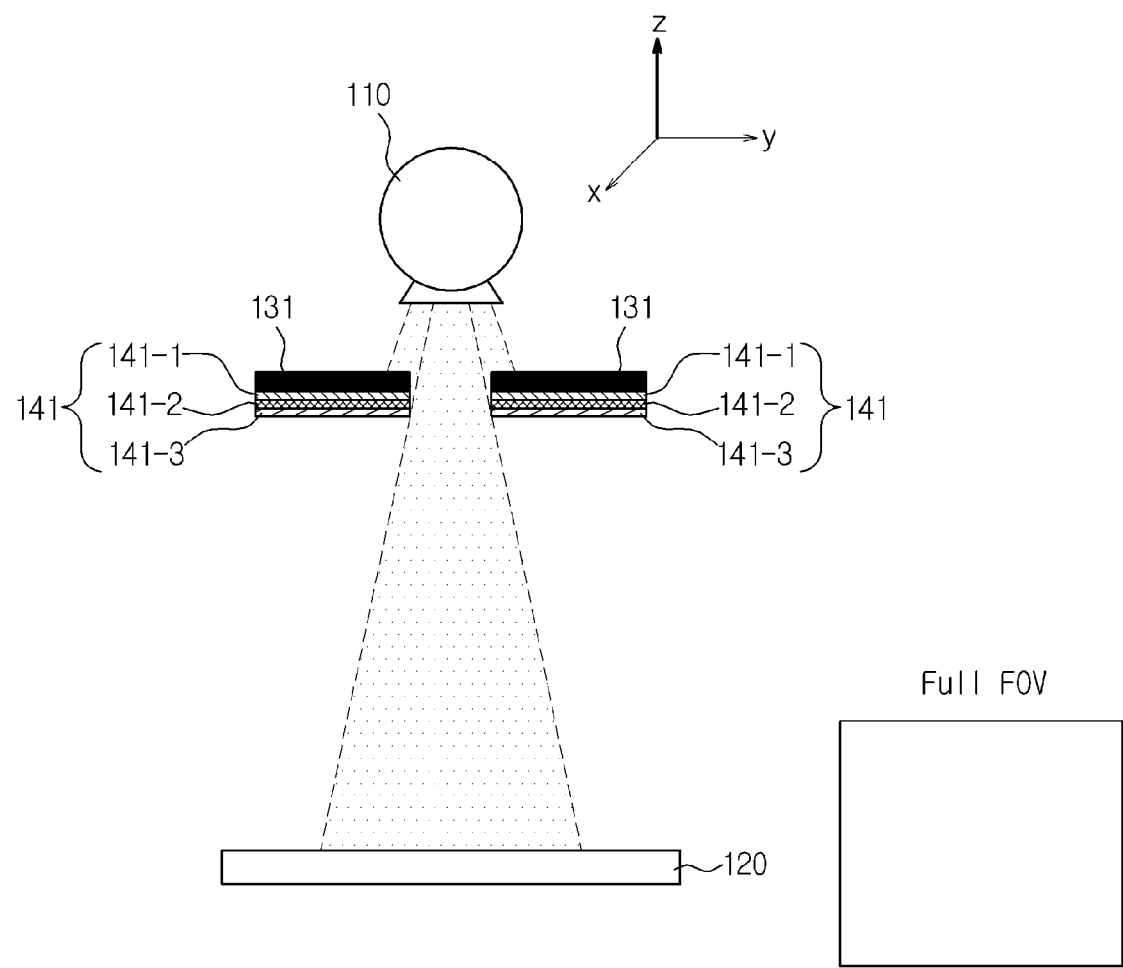

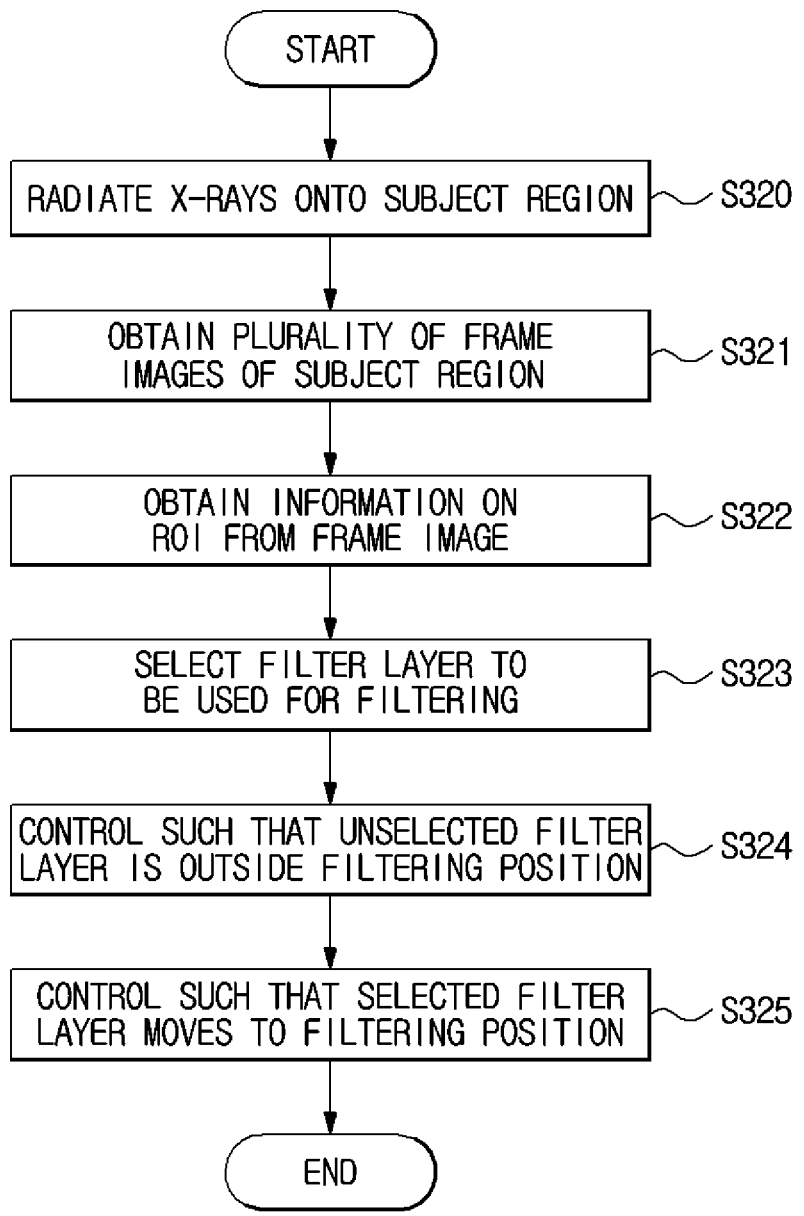

X-RAY IMAGING APPARATUS AND METHOD OF CONTROLLING THE SAME

CROSS-REFERENCE TO RELATED APPLICATION

This application claims priority from Korean Patent Application No. 10-2013-0140963, filed on Nov. 19, 2013 in the Korean Intellectual Property Office, the disclosure of which is incorporated herein by reference in its entirety.

BACKGROUND

1. Field

Apparatuses and methods consistent with the exemplary embodiments relate to an X-ray imaging apparatus that radiates X-rays onto a subject and images an inside thereof, and a method of controlling the same.

2. Description of the Related Art

An X-ray imaging apparatus is an apparatus capable of obtaining an internal image of a subject by radiating X-rays onto the subject and using X-rays transmitted through the subject to obtain an image. Since the permeability of X-rays differs depending on the properties of a substance which makes up the subject, an internal structure of the subject can be imaged by detecting an intensity or a strength of the X-rays transmitted through the subject.

However, increasing the safety of using the X-ray imaging apparatus by reducing an X-ray dose on the subject has become an important issue.

SUMMARY

Exemplary embodiments provide an X-ray imaging apparatus capable of implementing low dose X-ray imaging and minimizing field of view (FOV) loss of an X-ray image by allowing X-rays having a dose lower than that of a region of interest (ROI) to be incident on a non-ROI using an ROI filter, and a method of controlling the same.

Also, there are provided an X-ray imaging apparatus that can be applied to the field of an X-ray video by synchronizing movement of the ROI with movement of the ROI filter, and a method of controlling the same.

According to an aspect of an exemplary embodiment, there is provided an X-ray imaging apparatus. The apparatus includes an X-ray source configured to radiate X-rays onto a subject region; an X-ray detector configured to detect the radiated X-rays and obtain a plurality of frame images of the subject region; and a region of interest (ROI) filter located between the X-ray source and the X-ray detector to be movable toward the X-ray source and the X-ray detector, and configured to filter the X-rays radiated from the X-ray source.

The ROI filter may filter the X-rays radiated from the X-ray source so that X-rays having a dose lower than that of an ROI are incident on a non-ROI which is outside of the subject region.

The apparatus may further include a controller configured to control so that the filter moves in a three-dimensional (3D) space defined by an x-axis, a y-axis, and a z-axis according to a movement of the ROI or a size of the ROI.

According to another aspect of an exemplary embodiment, there is provided a method of controlling an X-ray imaging apparatus. The method includes radiating X-rays onto a subject region, detecting the radiated X-rays and obtaining information on a ROI which is outside of the subject region, and controlling a movement of an ROI filter configured to filter X-rays incident on a non-ROI which is outside of the subject region according to a movement of the ROI or a size of the ROI.

The movement of the filter is controlled so that the filter moves may include controlling the filter moves in a 3D space defined by an x-axis, a y-axis, and a z-axis according to movement of the ROI or the size of the ROI.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIGS. 11A to 11D are cross-sectional side views illustrating the ROI filter in which the plurality of layers independently move according to an exemplary embodiment;

FIG. 18 is a flowchart illustrating an exemplary embodiment of selecting a plurality of filter layers in the method of controlling an X-ray imaging apparatus according to an exemplary embodiment.

DETAILED DESCRIPTION

Hereinafter, exemplary embodiments of an X-ray imaging apparatus and a method of controlling the same will be described in detail with reference to the accompanying drawings.

Figure 1:
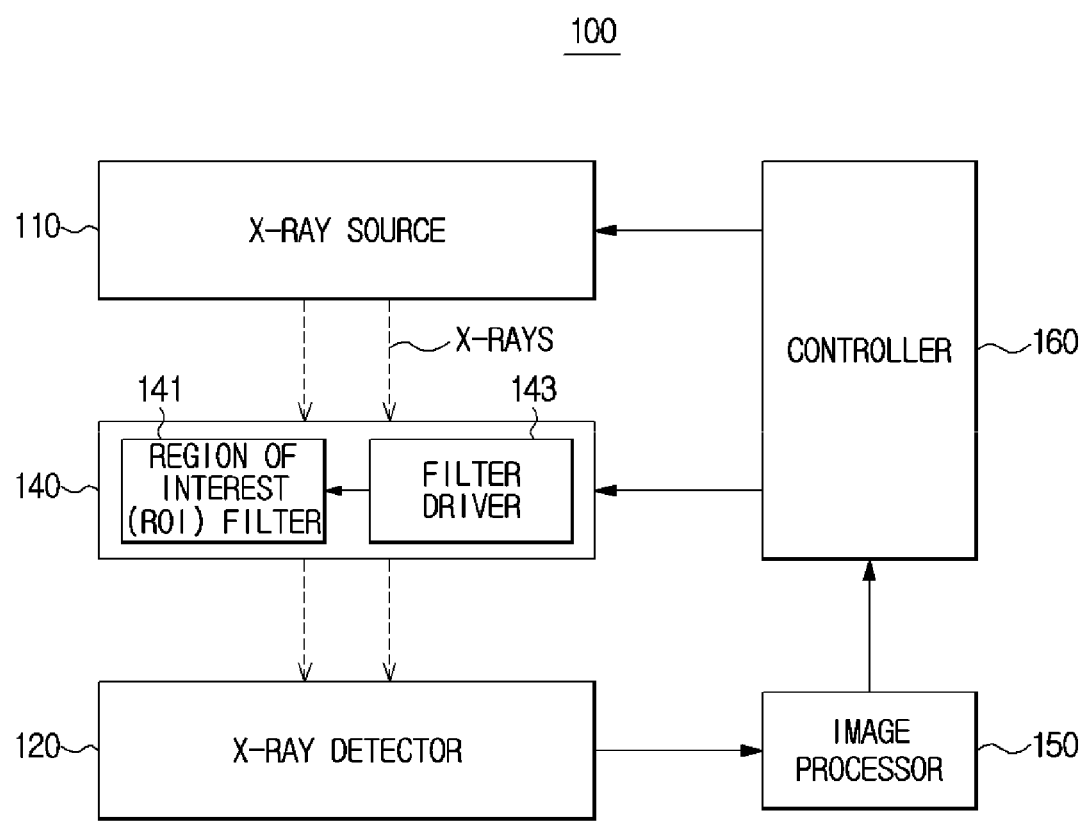
FIG. 1 is a control block diagram illustrating an X-ray imaging apparatus according to an exemplary embodiment.
Figure 2:
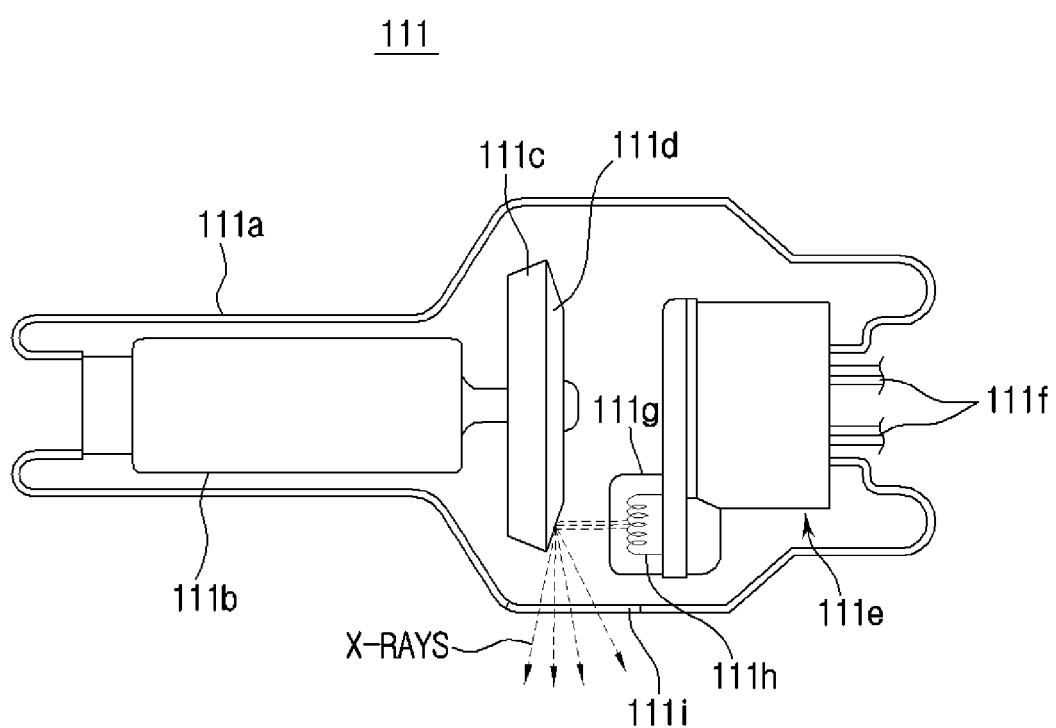
FIG. 2 is a cross-sectional view illustrating an internal structure of an X-ray tube included in the X-ray imaging apparatus according to an exemplary embodiment.

FIG. 1 is a control block diagram illustrating an X-ray imaging apparatus according to an exemplary embodiment. FIG. 2 is a cross-sectional view illustrating an internal structure of an X-ray tube included in the X-ray imaging apparatus according to the exemplary embodiment.

As illustrated in FIG. 1, an X-ray imaging apparatus 100 includes an X-ray source 110 configured to generate and radiate X-rays, an X-ray detector 120 configured to detect the radiated X-rays and obtain a frame image, a filtering unit 140 configured to filter the X-rays radiated from the X-ray source 110, an image processor 150 configured to detect a region of interest (ROI) from the obtained frame image, and a controller 160 configured to control the filtering unit 140.

As illustrated in FIG. 2, the X-ray source 110 may include an X-ray tube 111 configured to generate X-rays. An anode 111c and a cathode 111e are provided inside of a glass tube 111a of the X-ray tube 111. The inside of the glass tube 111a is maintained in a high vacuum state and thermoelectrons are generated by heating a filament 111h of the cathode 111e. The filament 111h may be heated by applying a current to an electrical conductor 111f connected to the filament.

The cathode 111e includes the filament 111h and a focusing electrode 111g configured to focus electrons. The focusing electrode 111g is also called a focusing cup.

When a high voltage is applied between the anode 111c and the cathode 111e, thermoelectrons are accelerated and collide with a target material 111d of the anode, and thereby X-rays are generated. High-resistance materials such as chromium (Cr), iron (Fe), cobalt (Co), nickel (Ni), tungsten (W), and molybdenum (Mo) may be used as the target material 111d of the anode. The generated X-rays are radiated externally through a window 111i. For example, a beryllium (Be) thin film may be used as a material of the window 111i. The target material 111d may be rotated by a rotor 111b.

The voltage applied between the anode 111c and the cathode 111e is referred to as a tube voltage, and a level thereof may be indicated as peak kilo-voltage (kvp). As the tube voltage increases, a rate of thermoelectrons increases. As a result, energy (photon energy) generated by the X-rays colliding with the target material increases. Energy of X-rays may also be adjusted by disposing a filter in a radiation direction of X-rays. A filter configured to filter X-rays of a specific wavelength band is positioned in front of or behind the window 111i, and thereby it is possible to filter X-rays of a specific wavelength band. For example, when a filter made of aluminum or copper is disposed, X-rays of a low-energy band are filtered and energy of radiating X-rays increases.

A current flowing in the X-ray tube 111, which is referred to as a tube current, may be indicated as an average mA, and may also be represented by a tube current level (mAs) that is the product of the tube current (mA) and an X-ray exposure time (s). As the tube current increases, the X-ray dose (the number of X-ray photons) increases. Therefore, energy of X-rays may be controlled by the tube voltage, and the X-ray dose may be controlled by the tube current and the X-ray exposure time, that is, the tube current level (mAs).

The X-ray imaging apparatus 100 may generate an X-ray video by applying fluoroscopy and may be applied in the field of X-ray diagnosis such as angiography or fields of various operations using the same. In this case, the X-ray video may be generated and displayed in real time.

The X-ray imaging apparatus 100 consecutively performs X-ray imaging in order to generate the X-ray video. A method of consecutively performing X-ray imaging includes a continuous exposure method and a pulse exposure method.

When the continuous exposure method is applied, a low tube current is continuously supplied to the X-ray tube 111 to continuously generate X-rays. When the pulse exposure method is applied, X-rays are generated by successive short pulses. Accordingly, when the pulse exposure method is applied, it is possible to decrease the X-ray dose and motion blurring. Any of the two methods may be applied to the X-ray imaging apparatus 100. For convenience of description, in the exemplary embodiment to be described below, the pulse exposure method may be applied.

The X-ray source 110 is able to radiate X-rays onto a subject region a plurality of times at predetermined time intervals or any time interval. Here, the predetermined time intervals or any time interval may be determined according to a pulse rate or a frame rate. The pulse rate may be determined by the frame rate, or vice versa. The frame rate may be set to 30 frames per second (fps), 5 fps, 7.5 fps, or the like. For example, when the frame rate is set to 15 fps, the pulse rate is set to 15 pps and thereby X-rays may be generated 15 times per second. If the pulse rate is set to 7.5 pps, X-rays may be generated 7.5 times per second.

The subject refers to an imaging target the inside of which will be represented by an X-ray image. The subject can be for example, a human or animal, or parts of the human or animal. The subject region is a specific region including the subject and refers to a region to be imaged as an X-ray image. Accordingly, the subject region matches an imaging region (field of view (FOV)) of the X-ray imaging apparatus 100 or may include the imaging region of the X-ray imaging apparatus 100.

The subject region includes at least one of the ROI and a non-ROI. A region other than the ROI out of the subject region is the non-ROI. The ROI and the non-ROI will be described in detail below.

The X-ray detector 120 detects X-rays and obtains a plurality of frame images of the subject region. The frame image refers to each of the plurality of X-ray images obtained according to the frame rate of the X-ray imaging apparatus 100. The X-ray detector 120 may have a two-dimensional (2D) array structure including a plurality of pixels. When the detected X-rays are converted into an electrical signal for each pixel, a single X-ray image of the subject region is obtained.

The X-ray detector 120 may apply any method of detecting X-rays and converting the X-rays into an electrical signal. For example, any method including a direct method in which X-rays are directly converted into an electrical signal using a photoconductor, such as amorphous-selenium (a-Se), and an indirect method in which X-rays are converted into visible light using a scintillator, such as a cesium iodide (CSI), and the visible light is converted into an electrical signal may be applied.

The filtering unit 140 includes an ROI filter 141 made of a material that absorbs X-rays and a filter driver 143 configured to move the ROI filter 141. The filter driver 143 may include a mechanical structure such as a motor configured to generate power, a gear configured to deliver the generated power to the ROI filter 141, and the like.

The ROI filter 141 may filter X-rays radiated from the X-ray source 110 such that X-rays having a dose lower than that of the ROI are incident on the non-ROI. This is performed in order to reduce the X-ray dose. Through X-ray filtering, X-rays having a dose higher than that of the non-ROI are applied to the ROI, in which useful information on an inside of the subject is included, and X-rays having a dose lower than that of the ROI are applied to the non-ROI, in which a small amount of information on the inside of the subject is included. Since X-rays are also incident on the non-ROI, there is no loss of the imaging region. A more detailed structure and operation of the filtering unit 140 will be described below.

As described above, the X-ray imaging apparatus 100 may obtain the X-ray video of the subject region by consecutively performing X-ray imaging. The frame images obtained by the X-ray detector 120 are input to the image processor 150. The image processor 150 may obtain information on the ROI by analyzing the input frame images. When the information on the ROI is delivered to the controller 160, the controller 160 controls the filtering unit 140 such that X-rays having a dose lower than that of the ROI are incident on the non-ROI.

Hereinafter, an operation of obtaining the information on the ROI of the image processor 150 will be specifically described.

First, the image processor 150 detects an object of interest from the frame image of the subject region. In order to detect the object of interest, characteristics of the object of interest are stored in advance, and an object corresponding to the pre-stored characteristic may be detected from the frame image of the subject region. From the characteristics of the object of interest, for example, a shape, an X-ray absorption characteristic, and a movement characteristic of the object of interest that can be detected from the X-ray image may be stored in advance. Here, the movement characteristic of the object of interest includes information on movement of the object of interest, and the information on the movement may include a movement direction, a movement speed, and a position change.

The object of interest refers to an object that the user of the imaging apparatus 100, such as a doctor or technician, continuously watches while X-ray imaging is performed and may be an instrument used for the subject or an operation site. If the X-ray imaging apparatus 100 is used for, for example, angiography, when the instrument such as a guide wire, a catheter, a needle, a balloon, or a stent is inserted into a blood vessel, careful observation of these instruments is necessary. Therefore, the instrument is set as the object of interest and information on a characteristic thereof may be stored in advance.

Also, when the operation site is set as the object of interest, a region of stenosis or aneurysm, or a cancerous region may be set as the object of interest.

When the object of interest is detected, the image processor 150 sets a specific region including the detected object of interest as the ROI. Therefore, a position and a size of the ROI may be determined in consideration of a position and a size of the object of interest or a movement characteristic of the object of interest.

Figure 3:
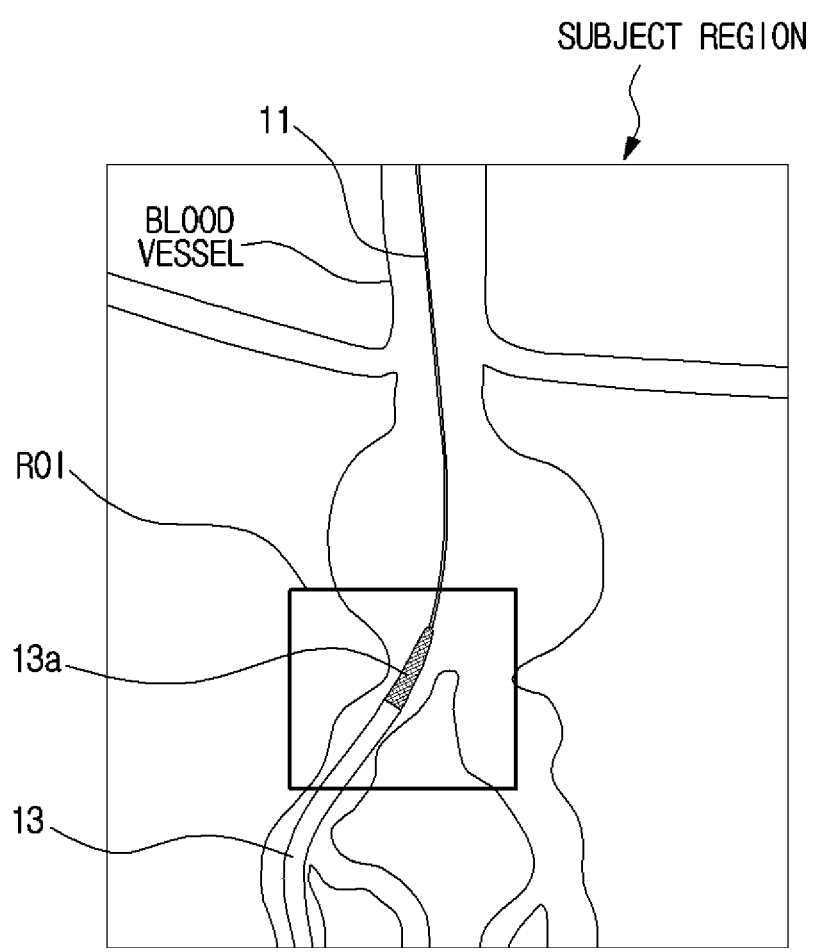
FIG. 3 is a diagram illustrating an exemplary region of interest (ROI) when a vascular stenting procedure is performed according to an exemplary embodiment.

FIG. 3 is a diagram illustrating an exemplary ROI when a vascular stenting procedure is performed according to an exemplary embodiment. Hereinafter, a specific example of setting the ROI will be described with reference to FIG. 3.

A stent 13a is inserted into the blood vessel in order to prevent obstruction of the blood vessel and the like, and the stent 13a has a mesh shape. The stent 13a is folded and installed at an end of a stent device 13 having a long tube shape, is introduced into the blood vessel, and is spread at a desired position in a mesh shape.

As illustrated in FIG. 3, in order to insert the stent device 13 into the blood vessel of the subject region, a guide wire 11 is inserted first. The stent device 13 is inserted into the blood vessel along the guide wire 11. While the stent device 13 is inserted, the stent device 13, and specifically, the stent 13a of a tip, may be the object of interest, and a specific region including the stent 13a may be the ROI.

While the guide wire 11 is inserted, the guide wire 11 or a tip of the guide wire 11 may be the object of interest. Although not illustrated in the drawing, when a catheter is inserted in order to inject a contrast agent into the blood vessel, the catheter or a tip of the catheter may be the object of interest.

Alternatively, the image processor 150 may use information which is input, for example, by a user, to detect the object of interest. For example, when information on a kind of the instrument, a kind of the operation, the operation site, injection of the contrast agent, and the like is input, it is possible to detect the object of interest from the frame image based on the input information.

For example, when information is input that an operation to be performed is an aortic stenting procedure and an instrument to be inserted is a stent device, the image processor 150 detects a stent inside of the aorta from the frame image of the subject region using the pre-stored information on the characteristics of the stent.

The image processor 150 may determine the movement characteristic of the object of interest while tracking the detected object of interest. Detecting and tracking of the object of interest, and obtaining the information on the ROI including the object of interest may be performed in real time according to the frame rate of the frame images input to the image processor 150. Here, obtaining the information on the ROI includes detecting and tracking of the object of interest and setting the ROI based on the result thereof.

The movement characteristic of the object of interest includes information on a movement size, a movement direction, and the like of the object of interest. The movement of the object of interest includes motion of the object of interest. The movement size may include a speed, but the movement of the object of interest may have no constant pattern. Therefore, the movement size may include various pieces of information indicating a movement degree in addition to the speed.

The ROI is a specific region including the object of interest and is defined by the object of interest. Therefore, the movement characteristic of the ROI may be determined by the movement characteristic of the object of interest.

Then, the information on the ROI obtained by the image processor 150, and specifically, information on the position, the size, or the movement characteristic of the ROI, is transmitted to the controller 160 and is used to control the filtering unit 140.

Also, the image processor 150 may obtain information on image characteristics represented in the frame image, such as noise and contrast. These characteristics may be transmitted to the controller 160, used to control X-ray imaging conditions, or may be used to determine a difference between X-ray doses incident on the ROI and the non-ROI. This will be further described below.

When the image processor 150 analyzes the frame image of the subject region and obtains the information on the ROI as described above, the ROI filter 141 in which movement thereof is controlled by the controller 160 filters X-rays incident on the non-ROI such that low dose X-rays are incident on the non-ROI.

Figure 4A:
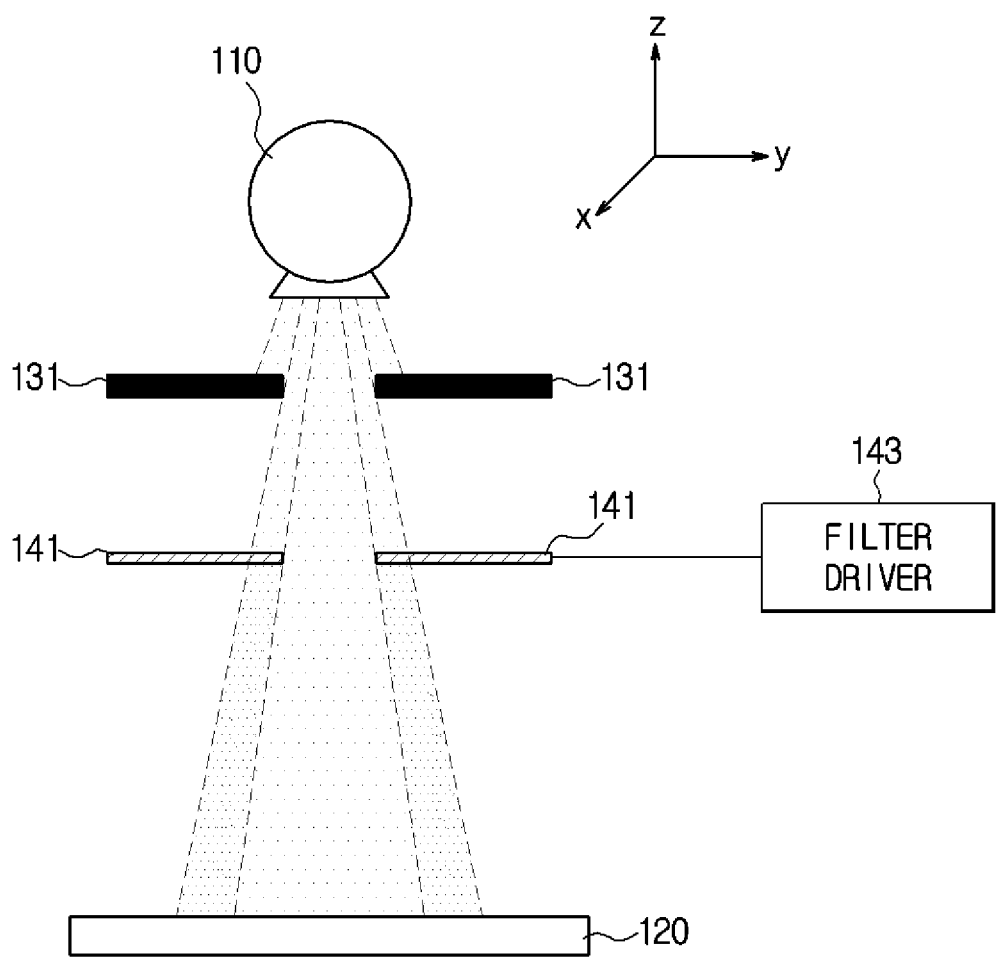
FIG. 4A is a cross-sectional side view of an ROI filter.
Figure 4B:
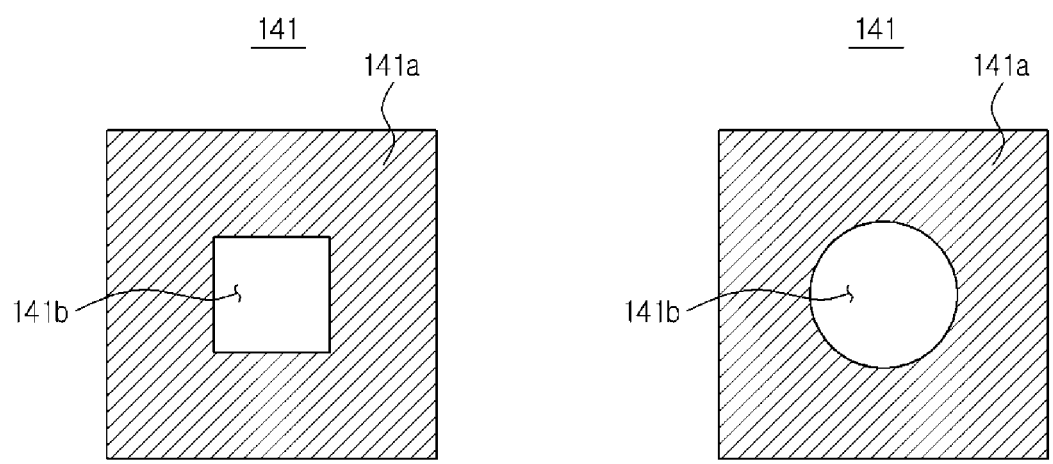
FIG. 4B is a plan view of an exemplary ROI filter according to an exemplary embodiment.

FIG. 4A is a cross-sectional side view of an ROI filter, and FIG. 4B is a plan view of an exemplary ROI filter according to an exemplary embodiment.

As illustrated in FIG. 4A, a collimator 131 may be disposed in an X-ray radiation direction corresponding to a front of the X-ray source 110. The collimator 131 is made of a material, such as lead or tungsten, that absorbs or blocks X-rays, adjusts a range of the imaging region (FOV) corresponding to an X-ray radiation region of the X-ray source 110, and reduces X-ray scattering.

The ROI filter 141 is positioned between the collimator 131 and the X-ray detector 120, and may filter X-rays incident on the non-ROI out of X-rays radiated from the X-ray source 110. The ROI filter 141 may be made of a material that reduces X-rays. Various materials having an X-ray attenuation characteristic such as aluminum (Al), copper (Cu), zirconium (Zr), molybdenum (Mo), silver (Ag), iridium (Ir), iron (Fe), tin (Sn), gold (Pt), platinum (Au), and tantalum (Ta), or a mixture therebetween may be used to form the ROI filter 141. The material having such an X-ray attenuation characteristic may be referred to as a filtration material.

The ROI filter 141 moves in a 3D space defined by x, y, and z axes and may be positioned at a position corresponding to the non-ROI. Here, the z-axis corresponds to a vertical line connecting the X-ray source 110 and the X-ray detector 120, and the x-axis and the y axis are perpendicular to the z-axis.

For example, the ROI filter 141 may move on an x-y plane or along the z-axis. Moving on the x-y plane is performed to allow the position of the non-ROI to correspond with the ROI filter 141. Moving along the z-axis or moving in a z-axis direction is performed to allow the size of the ROI to correspond with the ROI filter 141.

In general, since the ROI is surrounded by the non-ROI, as illustrated in FIG. 4B, the ROI filter 141 may have a shape having an empty center therein, and more specifically, a ring shape in which an opening 141b is formed at a center. The vicinity of the opening 141b is surrounded by a filtration material 141a.

The shape of the ROI filter 141 may have a ring shape in which the opening 141b is a polygon such as a rectangular as illustrated on the left in FIG. 4B and may have a ring shape in which the opening 141b is a circle as illustrated on the right in FIG. 4B, but an exemplary embodiment is not limited thereto. The ROI filter 141 may have various shapes according to the characteristic of the ROI, a geometric relation between the ROI and the non-ROI, and the like.

While X-rays flow into a certain material, when a dose of the X-rays is reduced or the X-rays are filtered, it may be represented that X-rays are transmitted through the material. When X-rays maintain the same property as before, X-rays flow into a corresponding material without reduction of a dose thereof or filtering, it may be represented that X-rays passes through the material.

Out of X-rays radiated from the X-ray source 110, a dose of X-rays incident on the filtration material 141a is reduced while the X-rays are transmitted through the filtration material 141a, and a dose of X-rays incident on the opening 141b is maintained while passing through the opening 141b. Accordingly, when the ROI filter 141, and more specifically, the filtration material of the ROI filter 141 is positioned at a position corresponding to the non-ROI of the subject region, X-rays having a dose lower than that of the ROI may be incident on the non-ROI. For example, an amount of X-rays incident on the non-ROI may be ⅕, ¹⁄₁₀ or ¹⁄₂₀ or less of an amount of X-rays incident on the ROI.

Figure 5A:
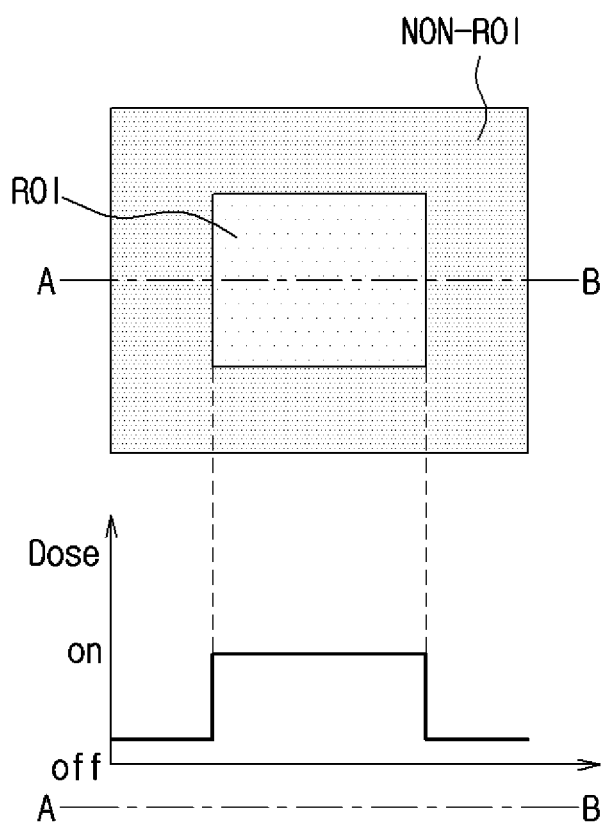
FIGS. 5A and 5B are diagrams schematically illustrating an X-ray dose incident on an ROI and a non-ROI according to an exemplary embodiment.
Figure 5B:
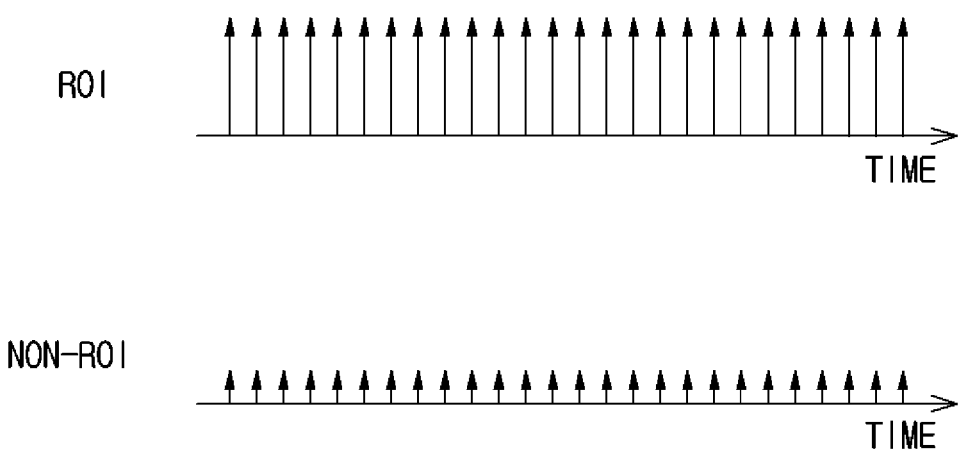

FIGS. 5A and 5B are diagrams schematically illustrating an X-ray dose incident on the ROI and the non-ROI.

FIG. 5A illustrates the X-ray dose incident on an arbitrary straight line AB which crosses the ROI and the non-ROI according to an exemplary embodiment. When the controller 160 moves the ROI filter 141 to the position corresponding to the non-ROI, as illustrated FIG. 5A, X-rays having a dose lower than that of the ROI are incident on the non-ROI. Since the X-rays are also incident on the non-ROI, though in a small amount, it is possible to obtain information on an entire imaging region.

As described above, the X-ray imaging apparatus 100 may obtain the video by consecutively performing X-ray imaging. The video is, for example, a fluoroscopic image which is a temporal series of X-ray images. X-ray image data can be obtained with a frame rate of 2-60 frames per second (fps) and can be presented on a display in real time. Therefore, the user, such as a doctor, can use the video to guide a device while performing, for example, an operation.

As long as the ROI is in the subject region, while a difference between X-ray doses incident on the ROI and the non-ROI is maintained as illustrated in FIG. 5B, X-ray imaging may be performed.

Figure 6A:
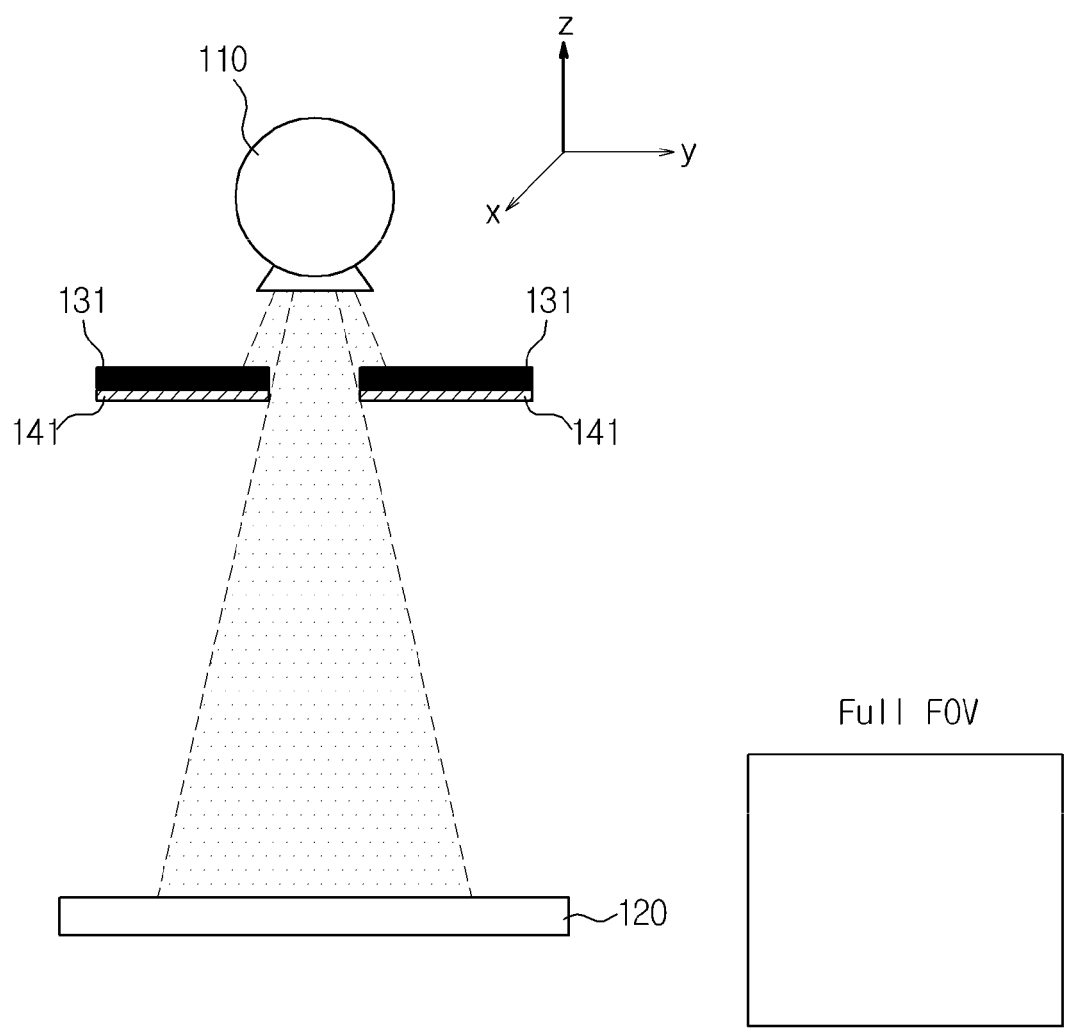
FIGS. 6A to 6C are diagrams illustrating an operation of controlling movement of the ROI filter along a z-axis according to a size of the ROI according to an exemplary embodiment.
Figure 6B:
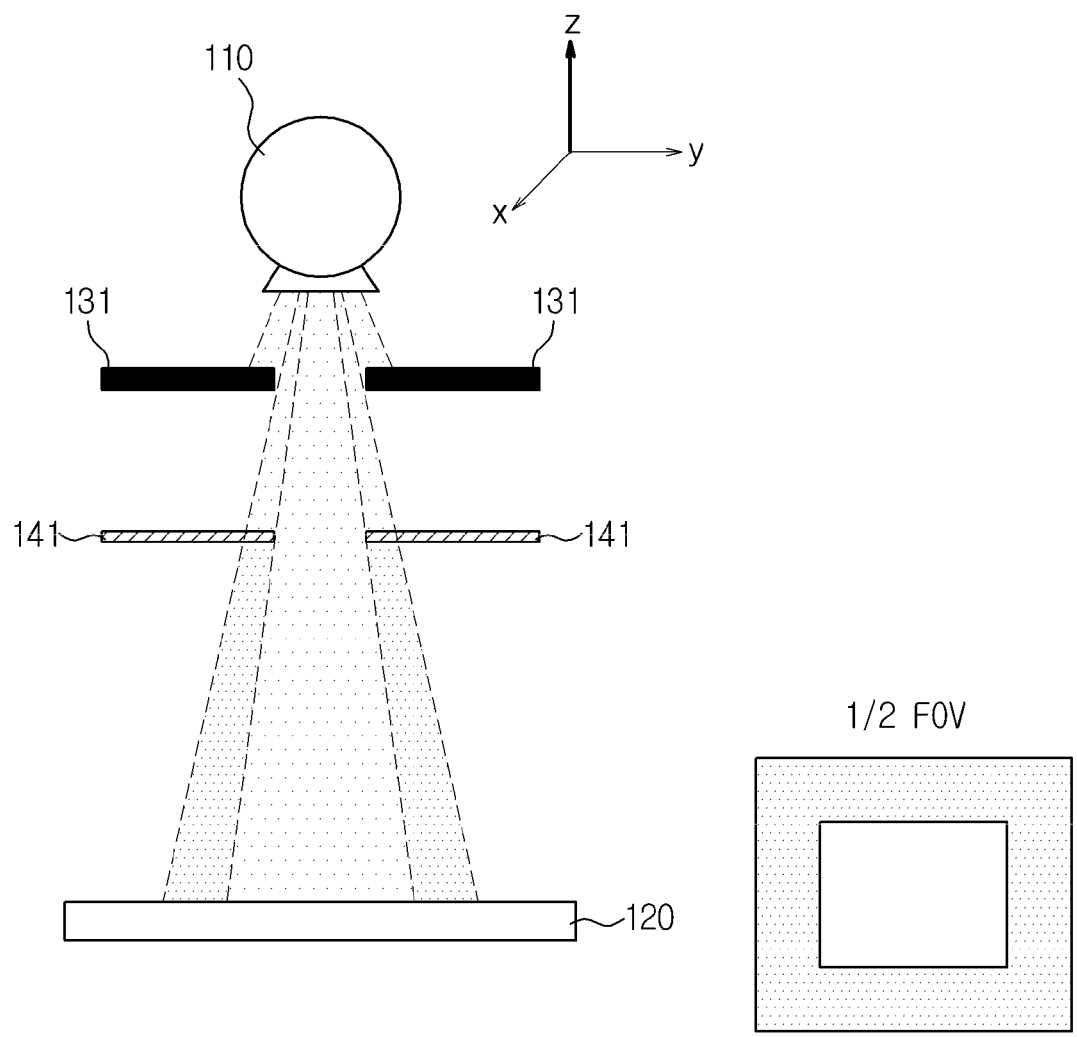
Figure 6C:
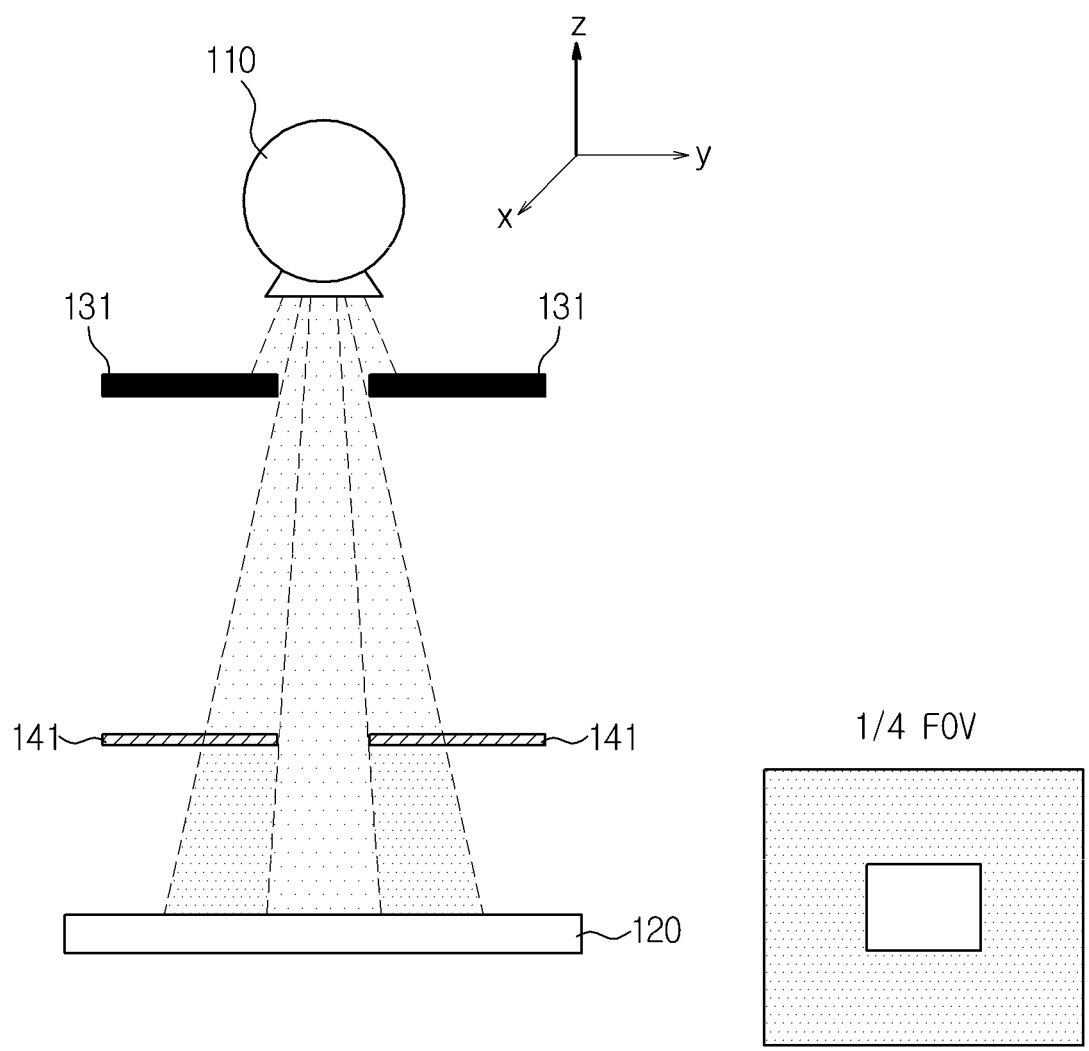

FIGS. 6A to 6C are diagrams illustrating an operation of controlling movement of the ROI filter along the z-axis according to the size of the ROI according to an exemplary embodiment.

Even though the X-ray imaging apparatus 100 includes the ROI filter 141, an image of the entire imaging region (full FOV) may be necessary. For example, when the movement of the object of interest is a predetermined reference value or more, when the contrast agent is injected into the blood vessel, or when an imaging mode of the X-ray imaging apparatus 100 is set as a digital subtraction angiography (DSA) mode to observe an entire image, X-rays having a uniform dose are incident on the entire imaging region.

In this case, when X-rays are to be emitted on the entire imaging region, as illustrated in FIG. 6A, the ROI filter 141 is positioned immediately below the collimator 131 and is outside a filtering position. Here, the filtering position refers to a position in which X-rays radiated from the X-ray source 110 or X-rays passing through the collimator 131 are filtered.

Specifically, the outmost X-rays of the X-rays which pass through the collimator 131 are introduced into the opening 141b of the ROI filter 141 and are outside of the filtering position. When the controller 160 causes the ROI filter 141 to be positioned immediately below the collimator 131 and outside of the filtering position, it is possible to obtain an image of the entire imaging region (Full FOV) in which X-rays passing through the collimator 131 are uniformly incident on the ROI and the non-ROI without distinction.

As described above, the controller 160 transmits a control signal to the filter driver 143, and then the filter driver 143 moves the ROI filter 141 in response to the transmitted control signal. However, for convenience of description, it may be described that the controller 160 moves the ROI filter 141.

When there is no need to obtain the image of the entire imaging region, as illustrated in FIGS. 6B and 6C, in order to allow only a low dose of X-rays to be incident on the non-ROI, the ROI filter 141 may be positioned at a filtering position.

Since X-rays radiated from the X-ray source 110 may generally have the form of a cone beam or a fan beam, as a surface on which X-rays are incident becomes further from the X-ray source 110, an area on which X-rays are incident increases. Accordingly, when the ROI filter 141, which has the opening 141b of a predetermined size, is positioned in front of the X-ray source 110, an area on which X-rays that pass through the opening 141b and are not filtered by the ROI filter 141 are incident differs according to a distance between the ROI filter 141 and the X-ray source 110.

Accordingly, the controller 160 controls the position of the ROI filter 141 along the z-axis according to the size of the ROI. In order to correspond the area on which X-rays, that are not filtered by the ROI filter 141 are incident with the size of the ROI, the controller 160 may control the movement of the ROI filter 141 along the z-axis.

Specifically, as exemplified in FIG. 6B, when the size of the ROI is ½ of the imaging region (½ of FOV), the controller 160 calculates the position of the ROI filter 141 along the z-axis corresponding thereto, and moves the ROI filter 141 to the calculated position. As illustrated in FIG. 6A, when the ROI filter 141 before moving is positioned immediately below the collimator 131, the ROI filter 141 moves in a direction of the X-ray detector 120 by a predetermined distance.

Also, as exemplified in FIG. 6C, when the size of the ROI is ¼ of the imaging region (¼ of FOV), the controller 160 calculates the position of the ROI filter 141 along the z-axis corresponding thereto, and moves the ROI filter 141 to the calculated position. When the ROI filter 141 before moving is positioned at the position as in FIG. 6B, the ROI filter 141 moves in the direction of the X-ray detector 120 by a predetermined distance.

According to the examples in FIGS. 6A to 6C, the controller 160 causes the ROI filter 141 to be positioned further from the X-ray detector 120 as the size of the ROI becomes greater, and causes the ROI filter 141 to be positioned closer to the X-ray detector 120 as the size of the ROI becomes smaller. For this purpose, the controller 160 previously stores a relationship between the size of the ROI and the position of the ROI filter 141, and may calculate the position of the ROI filter 141 according to the size of the ROI, and particularly, the position along the z-axis, using the pre-stored relationship.

The ROI filter which is used in the exemplary embodiments can be determined based on a desired material and thickness of an ROI filter. The properties of the ROI filter can also be based on the desired X-ray attenuation and spectral distribution. Further, the selection of the ROI filter can be based on the desired dose and spectrum of the X-rays which enter the non-ROI area.

Figure 7A:
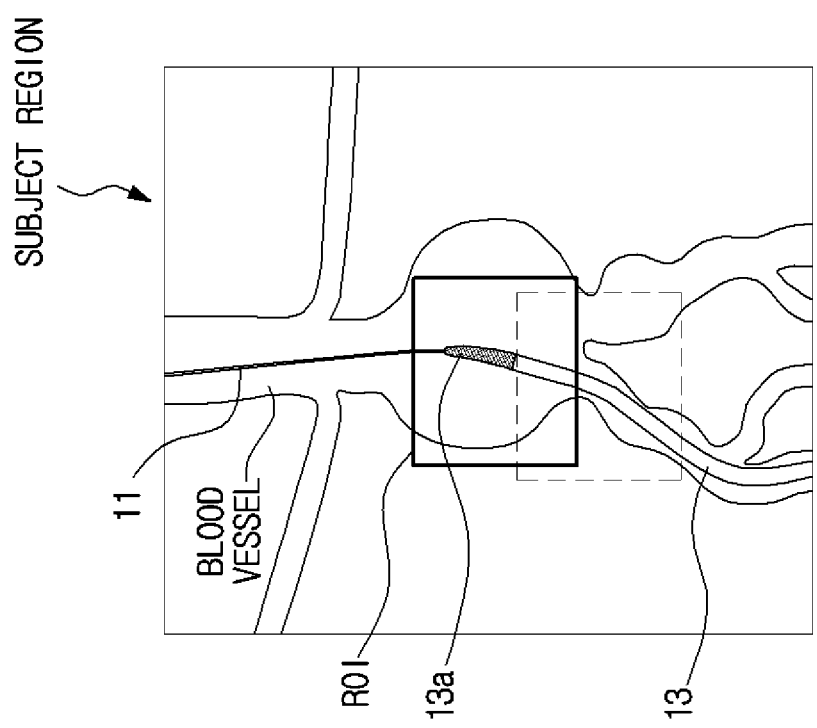
FIG. 7A is a diagram illustrating movement of the ROI according to movement of an object of interest.
Figure 7A:
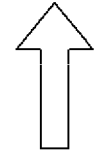
Figure 7A:
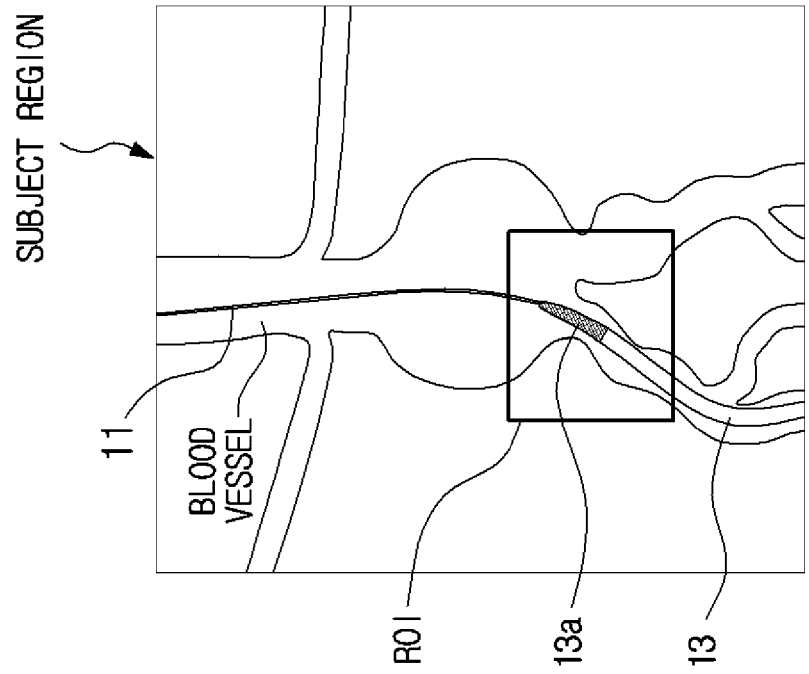
Figure 7B:
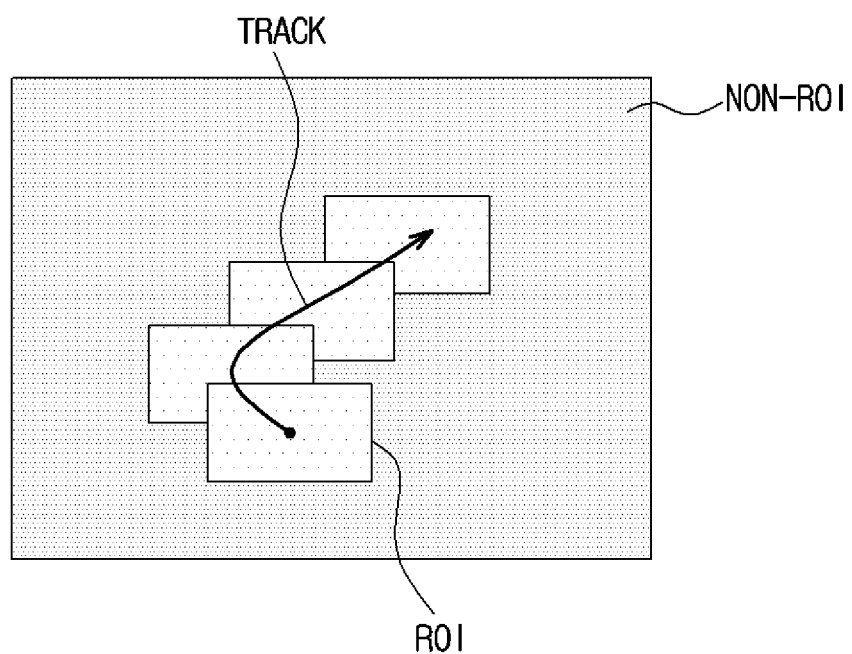
FIG. 7B is a diagram schematically illustrating an operation of tracking a moving ROI according to an exemplary embodiment.
Figure 8:
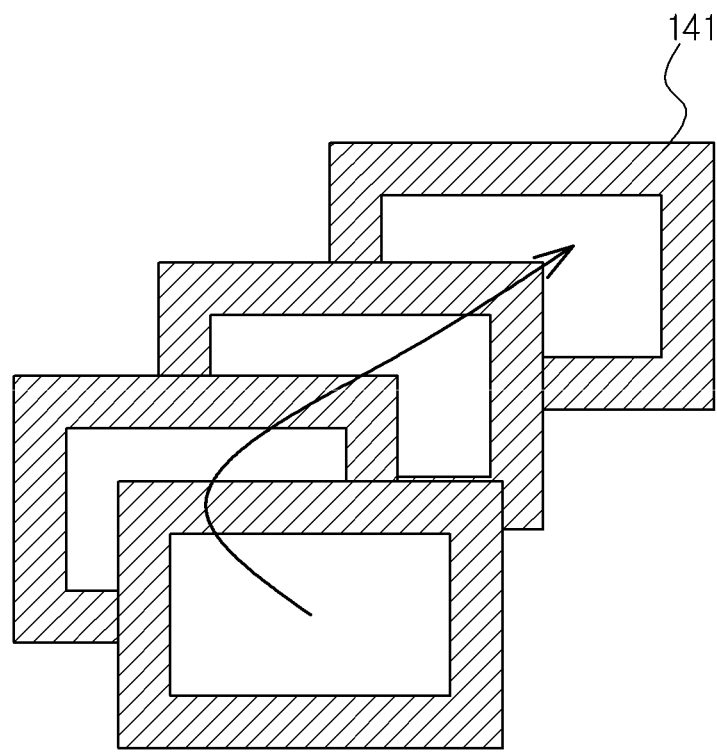
FIG. 8 is a diagram illustrating movement of the ROI filter according to movement of the ROI according to an exemplary embodiment.

FIG. 7A is a diagram illustrating movement of the ROI according to movement of the object of interest, and FIG. 7B is a diagram schematically illustrating an operation of tracking a moving ROI according to an exemplary embodiment. FIG. 8 is a diagram illustrating movement of the ROI filter according to movement of the ROI according to an exemplary embodiment.

The X-ray video may represent movement in the subject region. When a subject of the movement is the object of interest, the ROI may move according to the movement of the object of interest. For example, as illustrated in FIG. 7A, when the vascular stenting procedure is performed, the stent 13a serving as the object of interest moves to a target position inside the blood vessel and the ROI also moves according to the movement of the stent 13a.

As described above, the image processor 150 may detect and track the object of interest in real time. When the ROI moves, the image processor 150 tracks this movement in real time as illustrated in FIG. 7B, and the controller 160 moves the ROI filter 141 on the x-y plane as illustrated in FIG. 8 such that the position of the ROI or the non-ROI is synchronized with the position of the ROI filter 141.

While the ROI and the ROI filter 141 move together according to the movement of the object of interest in the examples in FIG. 7B and FIG. 8, the size of the ROI may also be changed according to the movement of the object of interest. For example, when the movement size of the object of interest is not large, in other words, when the movement size is a predetermined reference value or less, the image processor 150 may increase the size of the ROI according to the movement of the object of interest and may fix the position of the ROI. Since the ROI needs to include the moved object of interest while a position thereof is fixed, an increase rate of the size of the ROI may be changed according to the movement size of the object of interest.

In this case, the controller 160 does not move the ROI filter 141 on the x-y plane, and moves it only along the z-axis such that the position of the ROI filter 141 along the z-axis is synchronized with a change of the size of the ROI.

Figure 9:
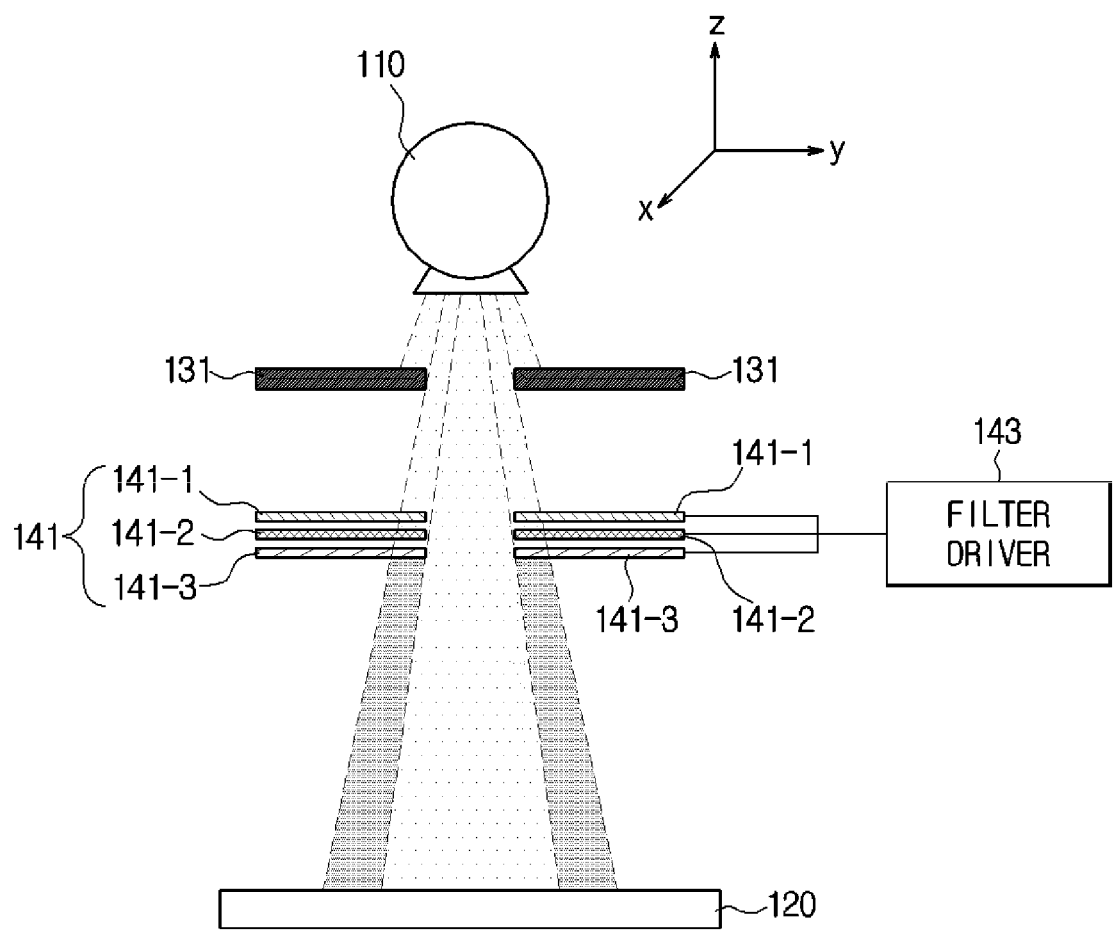
FIG. 9 is a cross-sectional side view of an ROI filter including a plurality of layers according to an exemplary embodiment.
Figure 10:
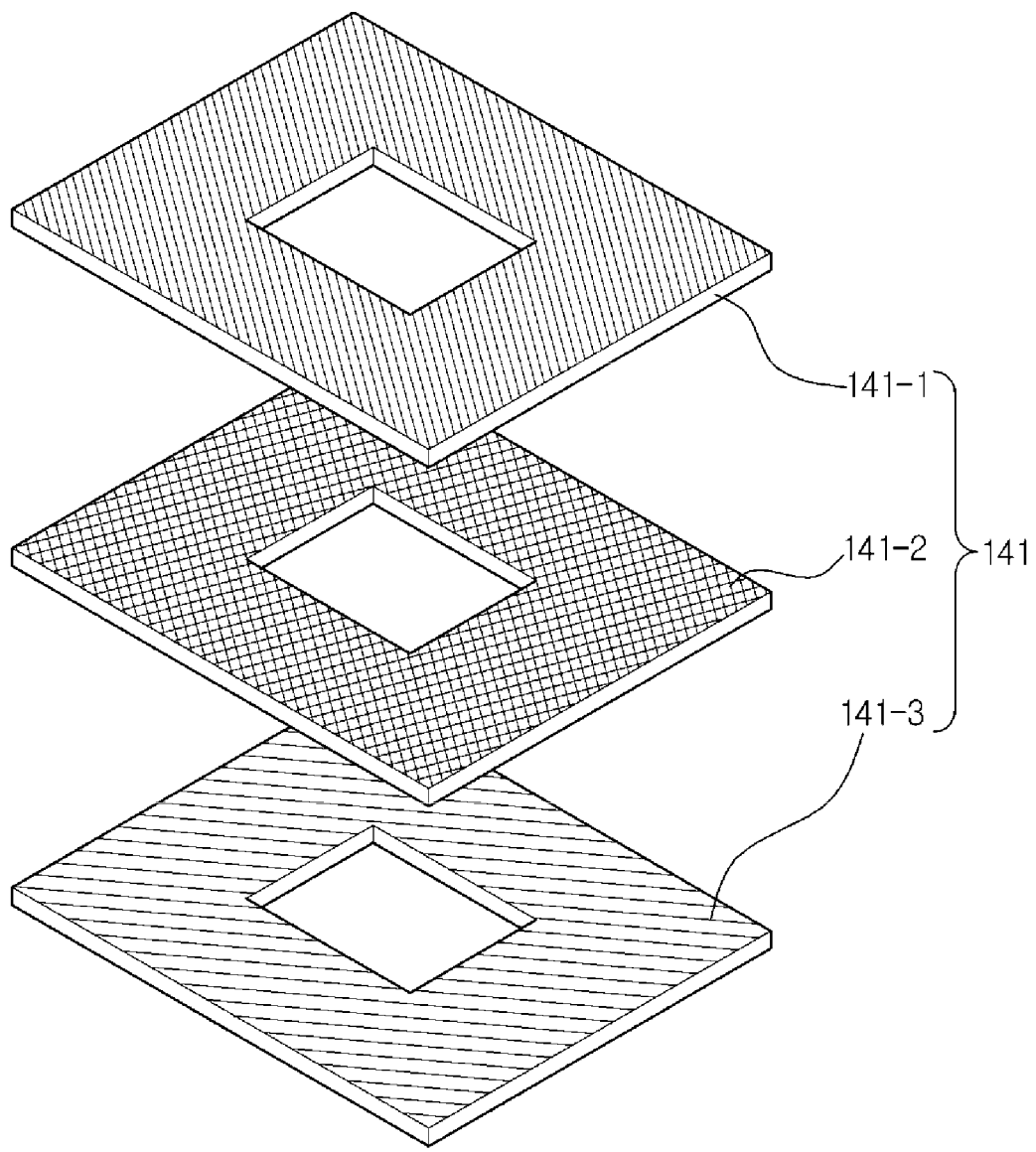
FIG. 10 is an exploded perspective view of the ROI filter including a plurality of layers as shown in FIG. 9, according to an exemplary embodiment.

FIG. 9 is a cross-sectional side view of an ROI filter including a plurality of layers according to an exemplary embodiment. FIG. 10 is an exploded perspective view of the ROI filter including a plurality of layers of FIG. 9, according to an exemplary embodiment.

The ROI filter 141 may include a plurality of filter layers that are independently movable on the x-y plane or along the z-axis. In the example of FIG. 9, three filter layers are included. The filter layers include a first ROI filter 141-1, a second ROI filter 141-2, and a third ROI filter 141-3. Although three filter layers are shown, the exemplary embodiments are not limited to three. Specifically, the number of layers used can be determined based on the desired X-ray attenuation. For example, by changing the number of layers, the amount of X-rays emitted in the non-ROI area can be modified.

The first ROI filter 141-1, the second ROI filter 141-2, and the third ROI filter 141-3 may have the same kind and the same thickness of the filtration material, the same kind but different thicknesses of the filtration material, both the kind and the thickness of the filtration material are different, or the same thickness but different kinds of filtration material in the examples in FIGS. 9 and 10.

The controller 160 may determine a difference between X-ray doses to be incident on the ROI and the non-ROI based on the information on the ROI. Here, the information on the ROI may further include image characteristics represented in the ROI and the non-ROI such as noise, motion, and contrast. According to the determined dose difference, it is possible to variably control the kind or the thickness of the ROI filter 141.

The controller 160 may control the X-ray dose to be incident on the non-ROI using a combination of the first ROI filter 141-1, the second ROI filter 141-2, and the third ROI filter 141-3. Hereinafter, a dose control operation using a combination of the filter layers will be described in detail with reference to FIGS. 11A to 12D.

FIGS. 11A to 11D are cross-sectional side views of the ROI filter in which the plurality of layers individually move according to an exemplary embodiment. In FIGS. 11A to 11D, movement of the ROI filter 141 is along the z-axis.

When the entire imaging region needs to be observed or when the movement of the object of interest is a predetermined reference value or more, as illustrated in FIG. 11A, all of the first ROI filter 141-1, the second ROI filter 141-2, and the third ROI filter 141-3 move in a direction of the X-ray source 110 and are outside the filtering position. Accordingly, it is possible to obtain an X-ray image of the entire imaging region.

Figure 11B:
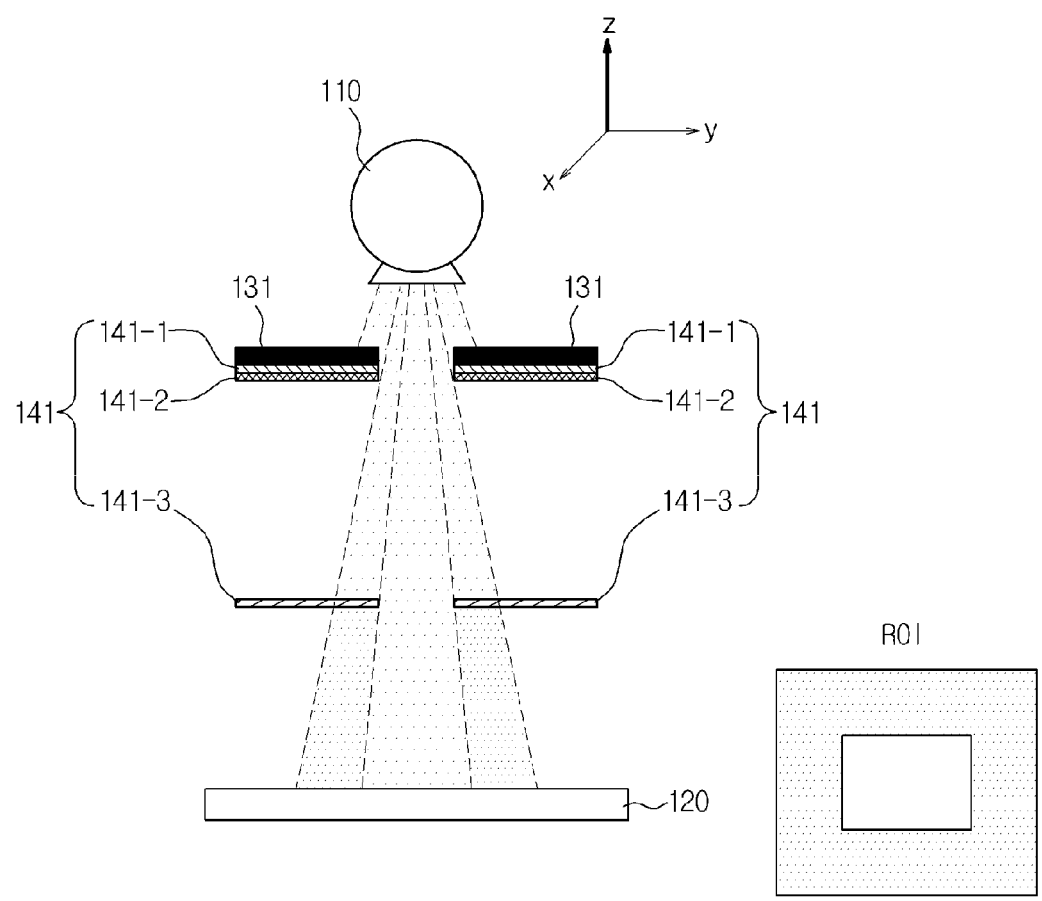

When a filter corresponding to the determined X-ray dose of the non-ROI is the third ROI filter 141-3, as illustrated in FIG. 11B, the first ROI filter 141-1 and the second ROI filter 141-2 move in the direction of the X-ray source 110 and outside of the filtering position, and the third ROI filter 141-3 moves to the filtering position matching the size of the ROI such that X-rays having a dose determined by the controller 160 are incident on the non-ROI.

Figure 11C:
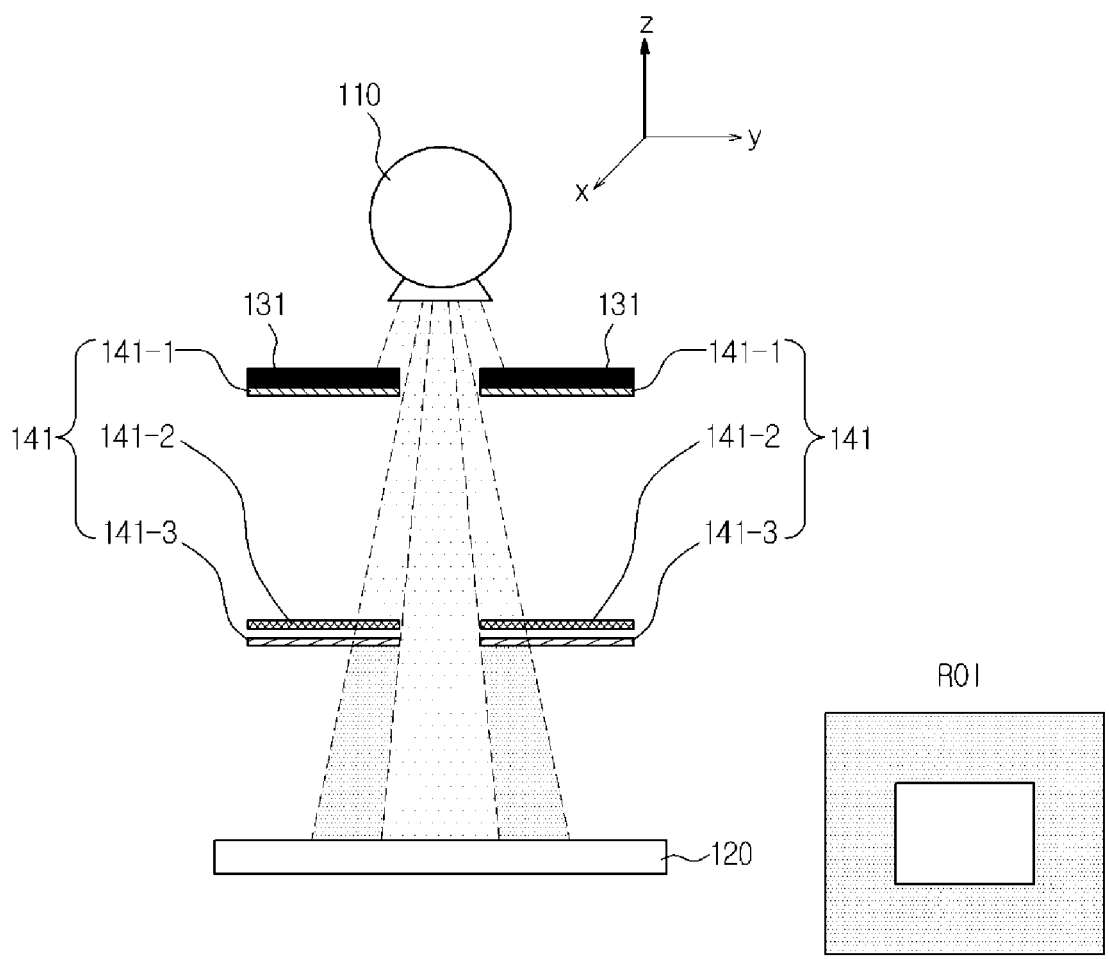

When a filter corresponding to the determined X-ray dose of the non-ROI is the second ROI filter 141-2 and the third ROI filter 141-3, as illustrated in FIG. 11C, the first ROI filter 141-1 moves in the direction of the X-ray source 110 and is outside the filtering position, and the second ROI filter 141-2 and the third ROI filter 141-3 move to the filtering position matching the size of the ROI so that X-rays having a dose determined by the controller 160 are incident on the non-ROI. In this case, since the second ROI filter 141-2 and the third ROI filter 141-3 perform filtering together, the X-ray dose incident on the non-ROI is further reduced compared to when only the third ROI filter 141-3 performs filtering.

Figure 11D:
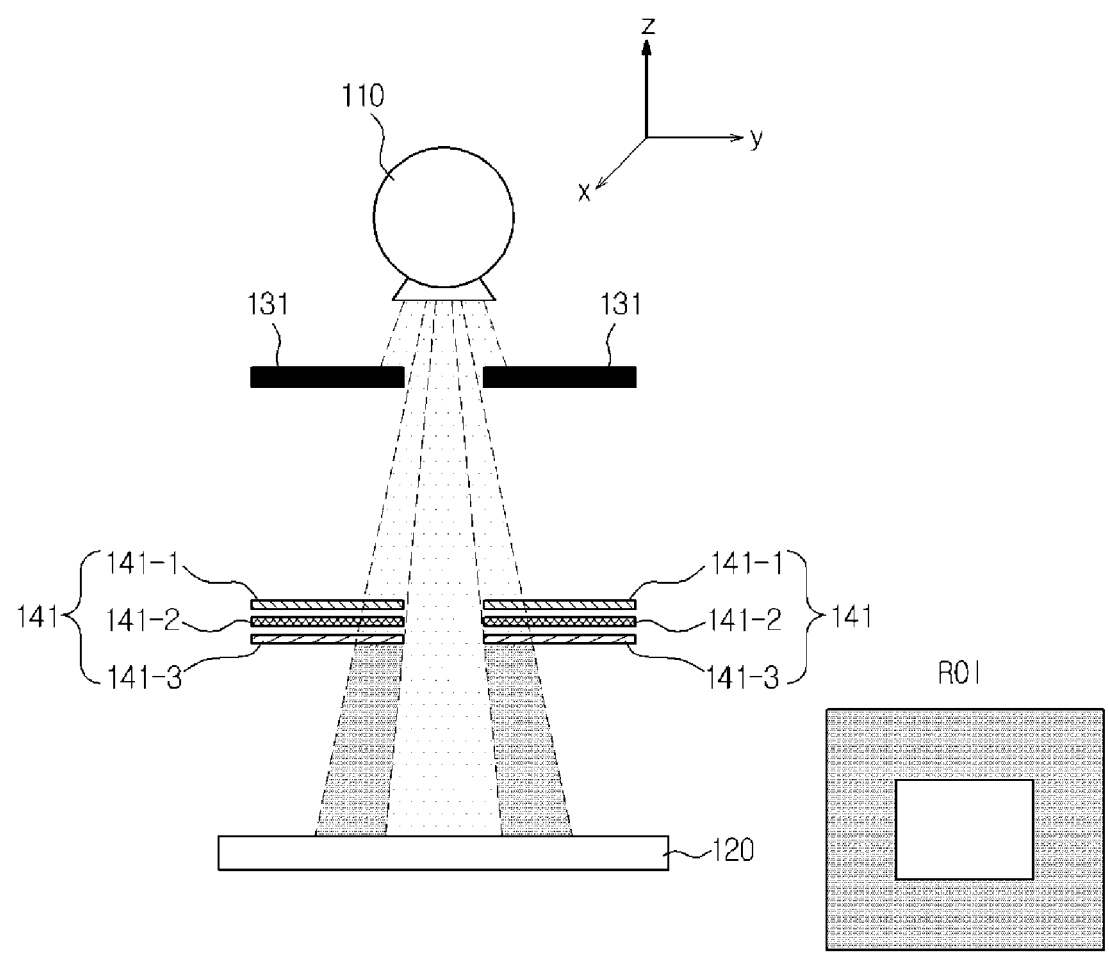

Otherwise, when a filter corresponding to the determined X-ray dose of the non-ROI is the first ROI filter 141-1, the second ROI filter 141-2, and the third ROI filter 141-3, as illustrated in FIG. 11D, all of the first ROI filter 141-1, the second ROI filter 141-2, and the third ROI filter 141-3 move to the filtering position matching the size of the ROI such that X-rays having a dose determined by the controller 160 are incident on the non-ROI. In this case, since all of the first ROI filter 141-1, the second ROI filter 141-2, and the third ROI filter 141-3 perform filtering, the X-ray dose incident on the non-ROI is further reduced compared to when the second ROI filter 141-2 and the third ROI filter 141-3 perform filtering or when only the third ROI filter 141-3 performs filtering.

While the ROI filter 141 moves in the direction of the X-ray source 110 along the z-axis is outside the filtering position in the above FIGS. 11A to 11D, the ROI filter 141 may also move on the x-y plane and be outside the filtering position. Hereinafter, this will be described with reference to FIGS. 12A to 12D.

FIGS. 12A to 12D are cross-sectional side views illustrating an operation in which the ROI filter moves on the x-y plane and the ROI filter is outside of the filtering position according to an exemplary embodiment.

Figure 12A:
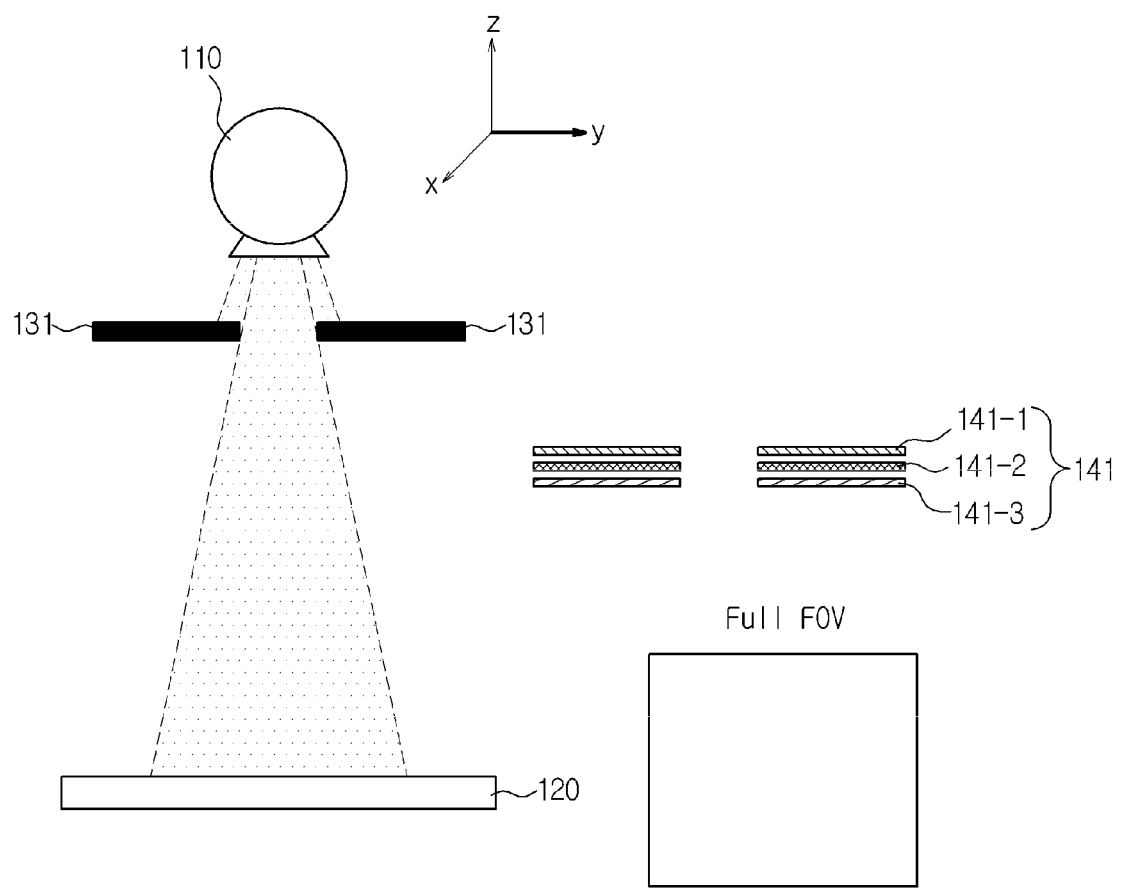
FIGS. 12A to 12D are cross-sectional side views illustrating an operation in which the ROI filter moves on an x-y plane and is outside of a filtering position according to an exemplary embodiment.

When the entire imaging region needs to be observed or when the movement of the object of interest is a predetermined reference value or more, as illustrated in FIG. 12A, all of the first ROI filter 141-1, the second ROI filter 141-2, and the third ROI filter 141-3 move on the x-y plane, for example, in a y axis direction, and are outside the filtering position. Therefore, it is possible to obtain an X-ray image of the entire imaging region.

Figure 12B:
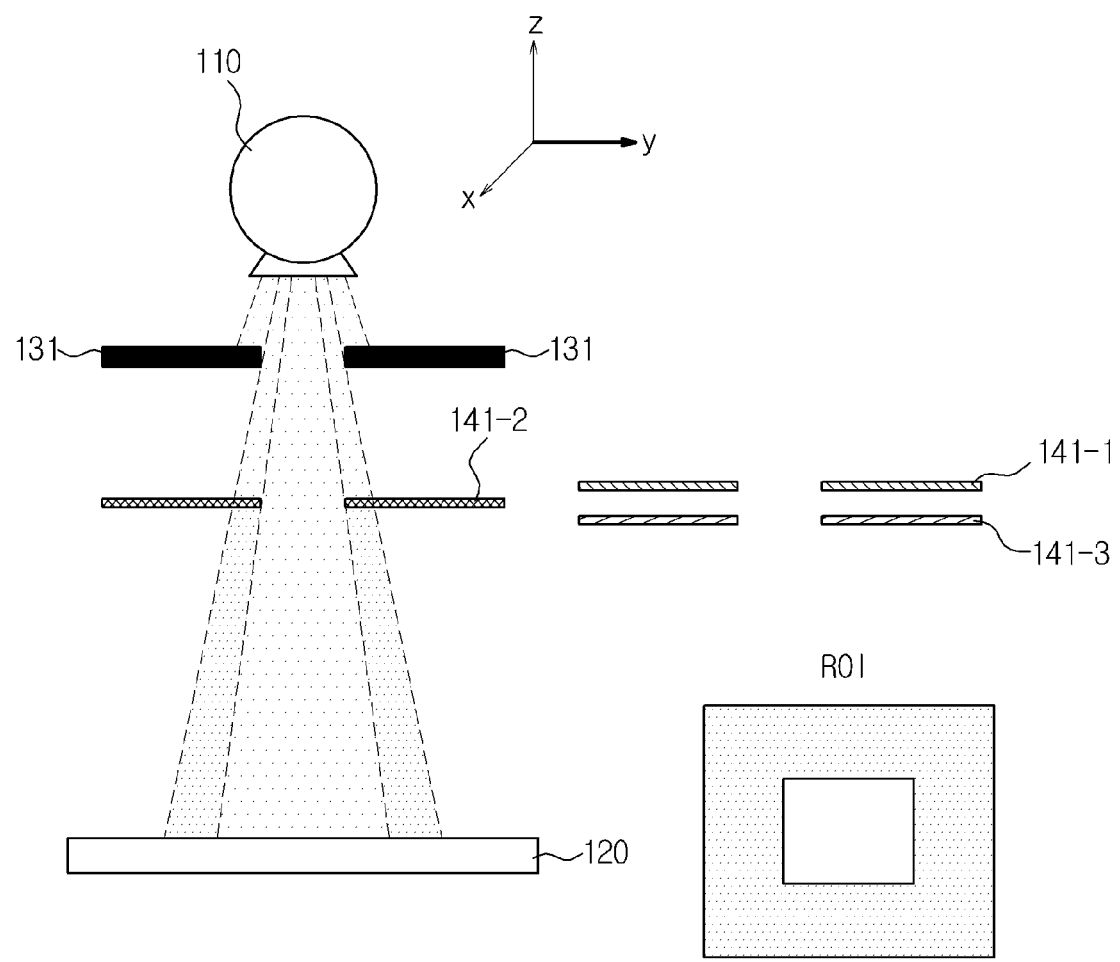

Otherwise, when a filter corresponding to the determined X-ray dose of the non-ROI is the second ROI filter 141-2, as illustrated in FIG. 12B, the first ROI filter 141-1 and the third ROI filter 141-3 move in the y axis direction and are outside the filtering position, and the second ROI filter 141-2 moves to the filtering position matching the size of the ROI so that X-rays having a dose determined by the controller 160 are incident on the non-ROI.

Figure 12C:
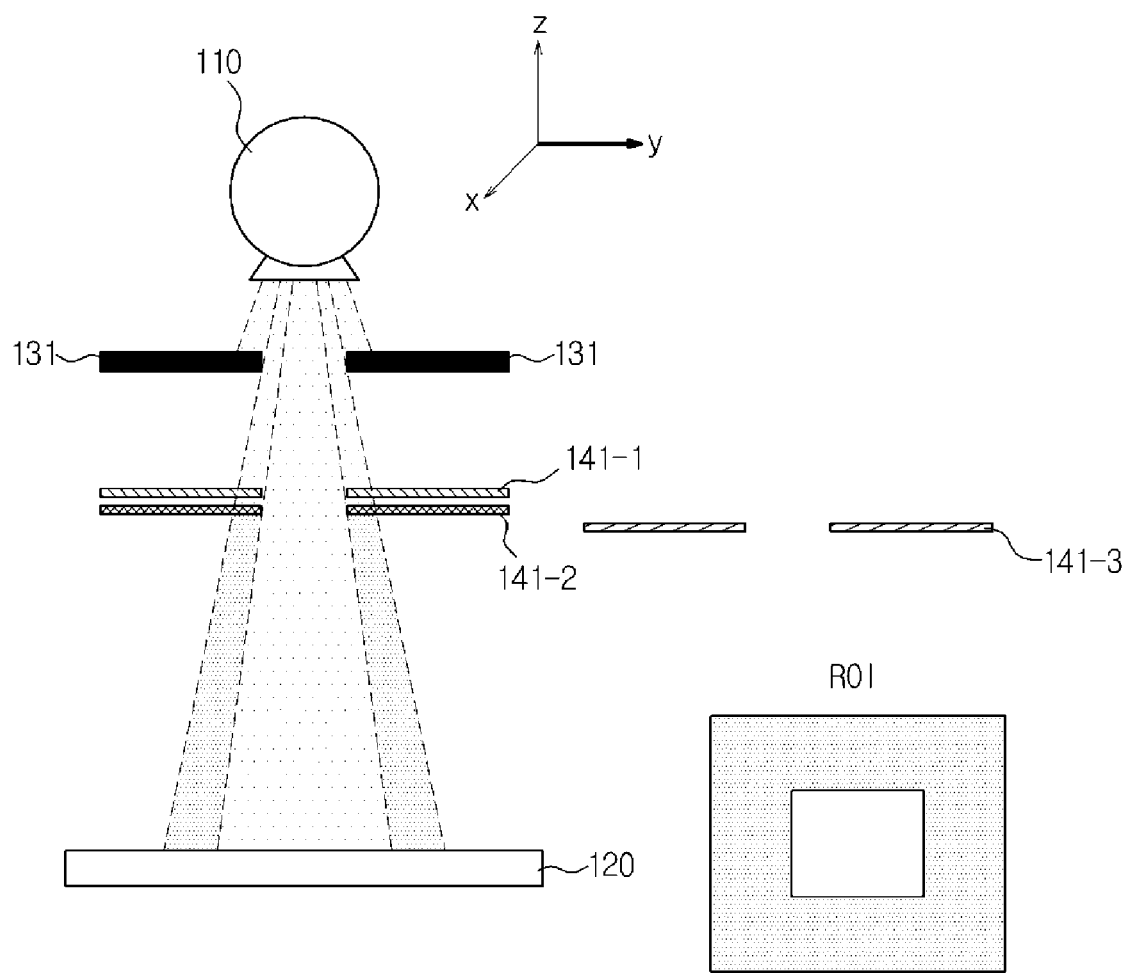

When a filter corresponding to the determined X-ray dose of the non-ROI is the first ROI filter 141-1 and the second ROI filter 141-2, as illustrated in FIG. 12C, the third ROI filter 141-3 moves in the y axis direction and are outside the filtering position, and the first ROI filter 141-1 and the second ROI filter 141-2 move to the filtering position matching the size of the ROI so that X-rays having a dose determined by the controller 160 are incident on the non-ROI.

Figure 12D:
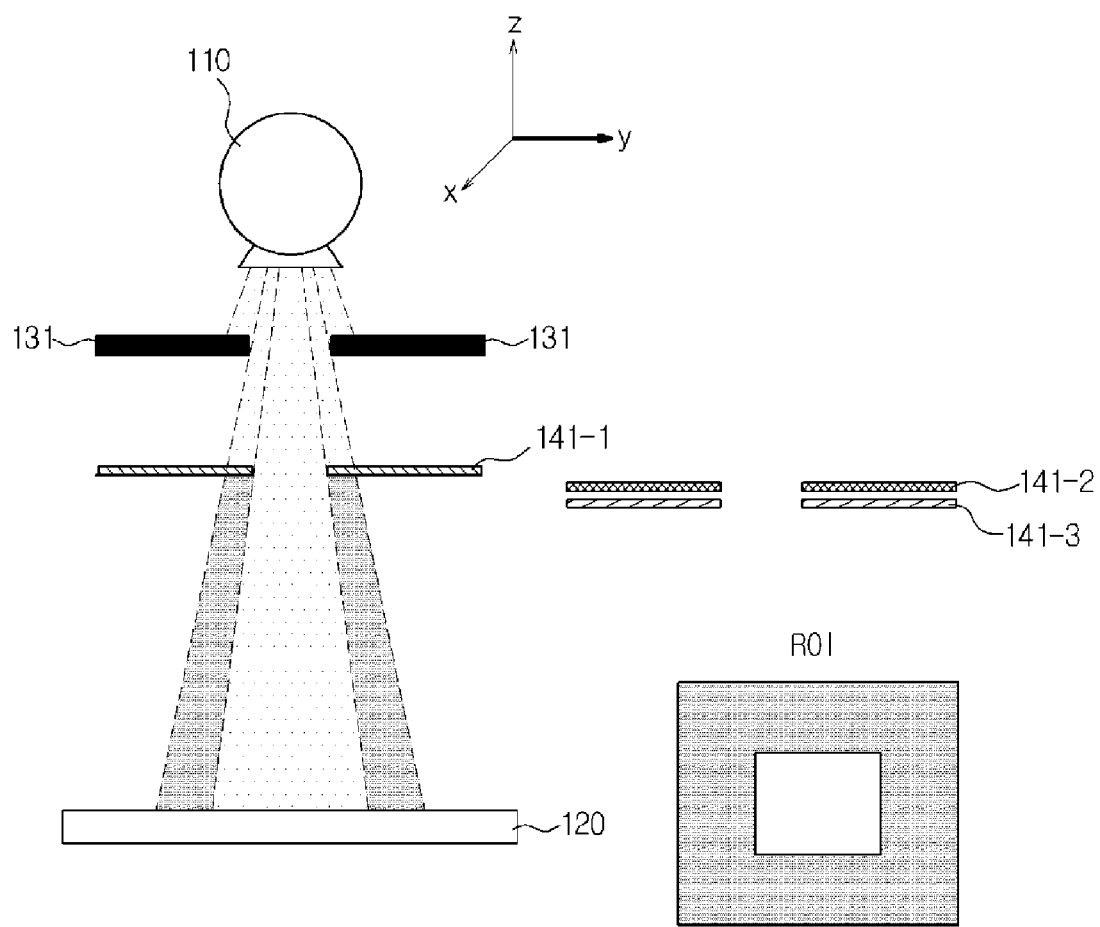

When a filter corresponding to the determined X-ray dose of the non-ROI is the first ROI filter 141-1, as illustrated in FIG. 12D, the second ROI filter 141-2 and the third ROI filter 141-3 move in the y axis direction and are outside the filtering position, and the first ROI filter 141-1 moves to the filtering position matching the size of the ROI so that X-rays having a dose determined by the controller 160 are incident on the non-ROI.

Figure 13A:
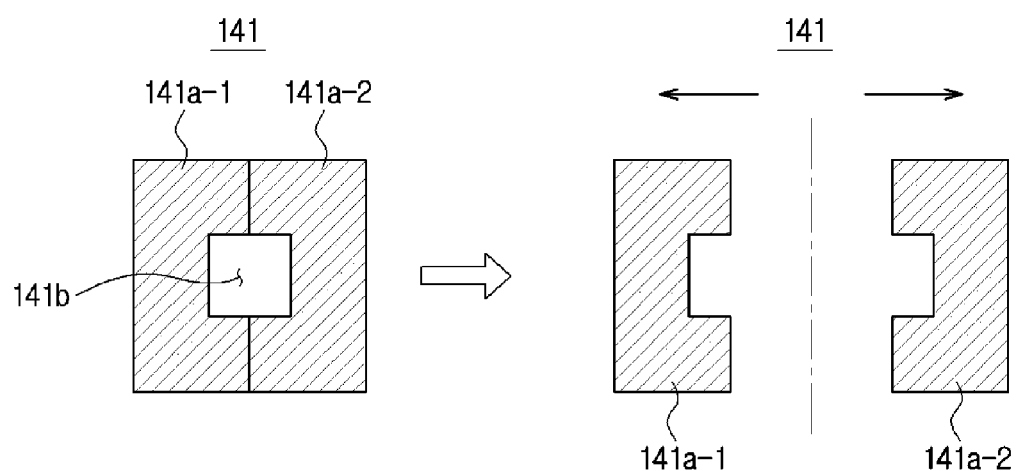
FIG. 13A is a plan view of a detachable ROI filter.
Figure 13B:
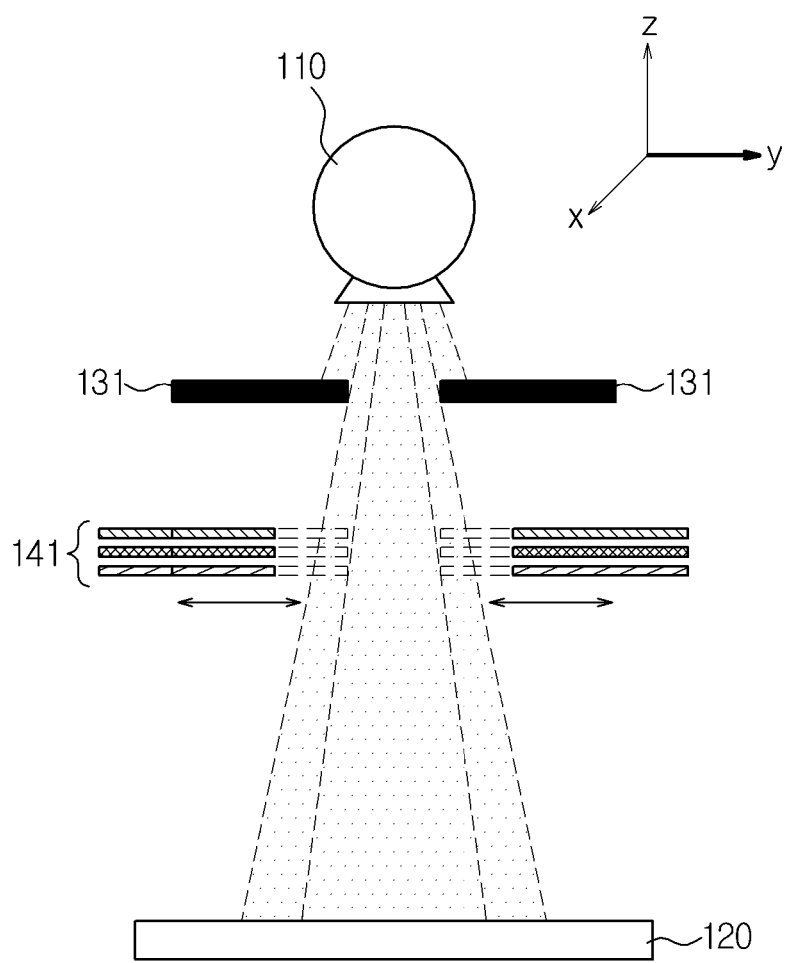
FIG. 13B is a diagram illustrating an operation in which detached ROI filters move on a y-axis in both directions and are outside of a filtering position according to an exemplary embodiment.

As another method of moving outside of the filtering position, the ROI filter 141 is implemented to be detachable and detached ROI filters 141 may move along the y axis in both directions as disclosed in FIGS. 13A and 13B.

FIG. 13A is a plan view of a detachable ROI filter, and FIG. 13B is a diagram illustrating an operation in which detached ROI filters move along the y axis in both directions and are outside the filtering position according to an exemplary embodiment.

As illustrated in FIG. 13A, the ROI filter 141 may be implemented to be detachable into two pieces 141a-1 and 141a-2. However, the pieces are not limited to two but the filter may be divided into three or more pieces as necessary.

As illustrated in FIG. 13B, the first ROI filter 141-1, the second ROI filter 141-2, and the third ROI filter 141-3 may be outside of the filtering position when the detached pieces move along the y axis in opposite directions. However, this is only an example, and it is sufficient if each of the detached pieces moves on the x-y plane further from the X-rays.

While all of the first ROI filter 141-1, the second ROI filter 141-2, and the third ROI filter 141-3 move in the example in FIG. 13B, the ROI filters may be independently movable.

Figure 14:
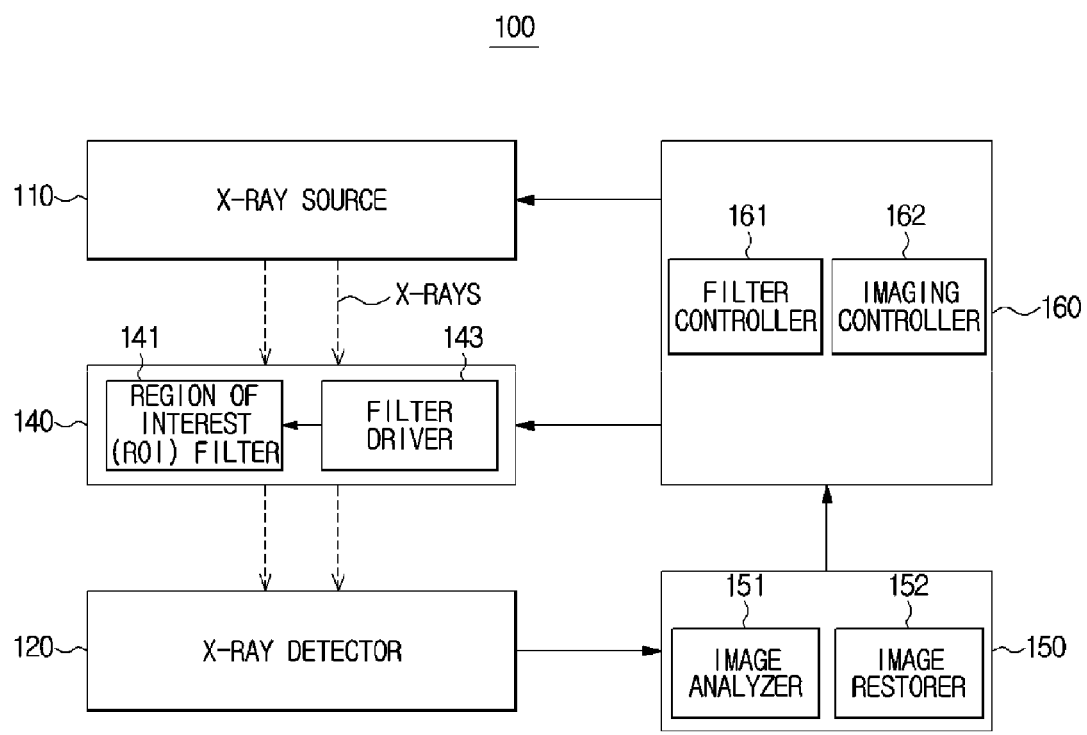
FIG. 14 is a control block diagram illustrating an X-ray imaging apparatus capable of restoring image quality of a frame image having an adjusted X-ray dose and controlling X-ray imaging parameters according to an exemplary embodiment.

FIG. 14 is a control block diagram illustrating an X-ray imaging apparatus capable of restoring the image quality of a frame image having an adjusted X-ray dose and controlling the X-ray imaging parameters according to an exemplary embodiment.

The image processor 150 may include an image analyzer 151 configured to obtain information on the ROI from the frame image or image characteristics represented in the ROI and the non-ROI of the frame image, and an image restorer 152 configured to restore the frame image.

When the X-ray dose is small, a signal-to-noise ratio (SNR) of the X-ray image may decrease. Accordingly, the image restorer 152 may restore a frame image obtained while X-rays having a dose lower than that of the ROI are incident on the non-ROI using at least one previous frame image.

The image restorer 152 may restore a current frame image by combining it with at least one previous frame image. Combining the frame images may be performed on the non-ROI.

Figure 15:
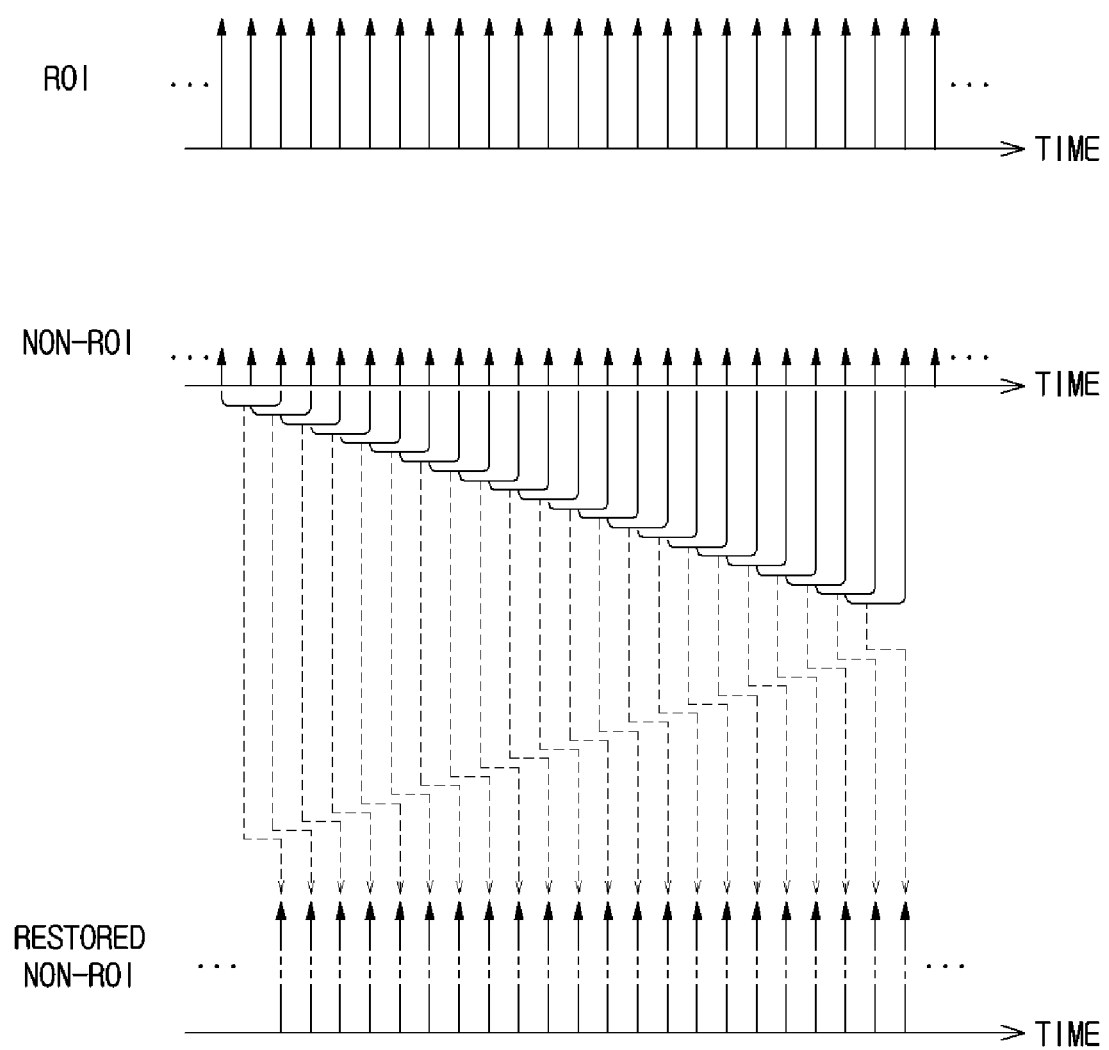
FIG. 15 is a diagram schematically illustrating restoration of image quality by combining frame images according to an exemplary embodiment.

FIG. 15 is a diagram schematically illustrating restoration of image quality by combining frame images according to an exemplary embodiment.

As illustrated in FIG. 15, the image restorer 152 restores a current frame image of the non-ROI by combining it with two previous frame images, and thereby it is possible to obtain a frame image having an excellent SNR, similar to the frame image of the ROI on which high-dose X-rays are incident.

Examples of a method of combining a current frame image and at least one previous frame image include a method of summing a current frame image and at least one previous frame image, a method of averaging a current frame image and at least one previous frame image, a method of changing a filter to be applied to a current frame image in consideration of image characteristics, such as an edge direction, a method of applying motion-compensated temporal filtering, and a method of applying motion-compensated spatial filtering. Here, the sum may be a simple sum or a weighted sum, and the average may be a simple average or a weighted average.

Also, the image restorer 152 may perform additional image enforcement on the non-ROI of the restored frame image. For example, in order to reduce degradation of the resolution and image blurring that can be generated when the current frame image and the previous frame image are combined, it is possible to perform alignment or registration between frame images, or motion prediction and compensation.

As an algorithm for registering between frame images, a characteristic-based algorithm, an intensity-based algorithm, or an algorithm in which a characteristic and an intensity are mixed may be used.

As a motion field model for motion prediction and compensation, translational motion, block-based piecewise translational motion, rotation, scaling, and non-rigid deformable motion may be used.

The image restorer 152 may also perform restoration work for improving the image quality on the ROI of the frame image. Specifically, the image restorer 152 may restore the ROI of the frame image using a de-noising algorithm such as a spatial filter, a temporal filter, a spatio-temporal filter, and super-resolution reconstruction.

Also, the image restorer 152 may enhance the ROI of the frame image using a detail enhancement algorithm, such as a contrast enhancement algorithm, based on a histogram or a wavelet, and an edge enhancement filter.

In addition, the image restorer 152 may perform an image equalization algorithm for matching brightness and contrast of the ROI and the non-ROI of the frame image.

The controller 160 includes a filter controller 161 configured to control the filtering unit 140 and an imaging controller 162 configured to control imaging parameters used for X-ray imaging.

The imaging controller 162 controls various imaging parameters applied during X-ray imaging. The imaging parameter is also called an exposure parameter. Automatically controlling the imaging parameters in the X-ray imaging apparatus 100 is called auto exposure control.

The imaging parameters may be at least one selected from the group including the tube voltage, the tube current, the exposure time, the kind of the filter, the imaging region (FOV), the frame rate, the pulse rate, and the kind of the target material.

The imaging parameter may be determined based on the frame image of the subject region and may also be determined based on prior information input before X-ray imaging begins. Hereinafter, an exemplary embodiment of the former case will be described in detail.

The imaging controller 162 may determine the imaging parameter based on an analysis result of the image analyzer 151. For example, when the image analyzer 151 analyzes the frame image and determines characteristics such as a thickness or a density of the subject, the imaging controller 162 may determine imaging parameters such as the tube voltage, the tube current, the exposure time, the kind of the filter, and the kind of the target material, which match the characteristics of the subject, based on the determination result.

Alternatively, the imaging controller 162 may also determine the imaging parameter based on the information on the ROI obtained by the image analyzer 151. For example, the imaging controller 162 may determine the imaging parameters such as the frame rate, the tube current, and a dose per frame according to the movement size of the object of interest or characteristics of the image represented in the ROI, and may control individually or simultaneously the imaging parameters.

For example, when the movement size of the object of interest is large, the imaging controller 162 increases the frame rate and obtains information on the movement of the object of interest maximally, and when the movement size of the object of interest is small, the imaging controller 162 decreases the frame rate and reduces X-ray exposure to the subject.

The imaging controller 162 may also control a dose per frame according to a noise level of the ROI. For example, when the noise level of the ROI is higher than a predetermined reference value, the dose per frame increases and the noise level decreases, thereby making the ROI to be shown more clearly. When the noise level of the ROI is lower than the predetermined reference value, the dose per frame decreases, thereby reducing X-ray exposure to the subject.

Figure 16:
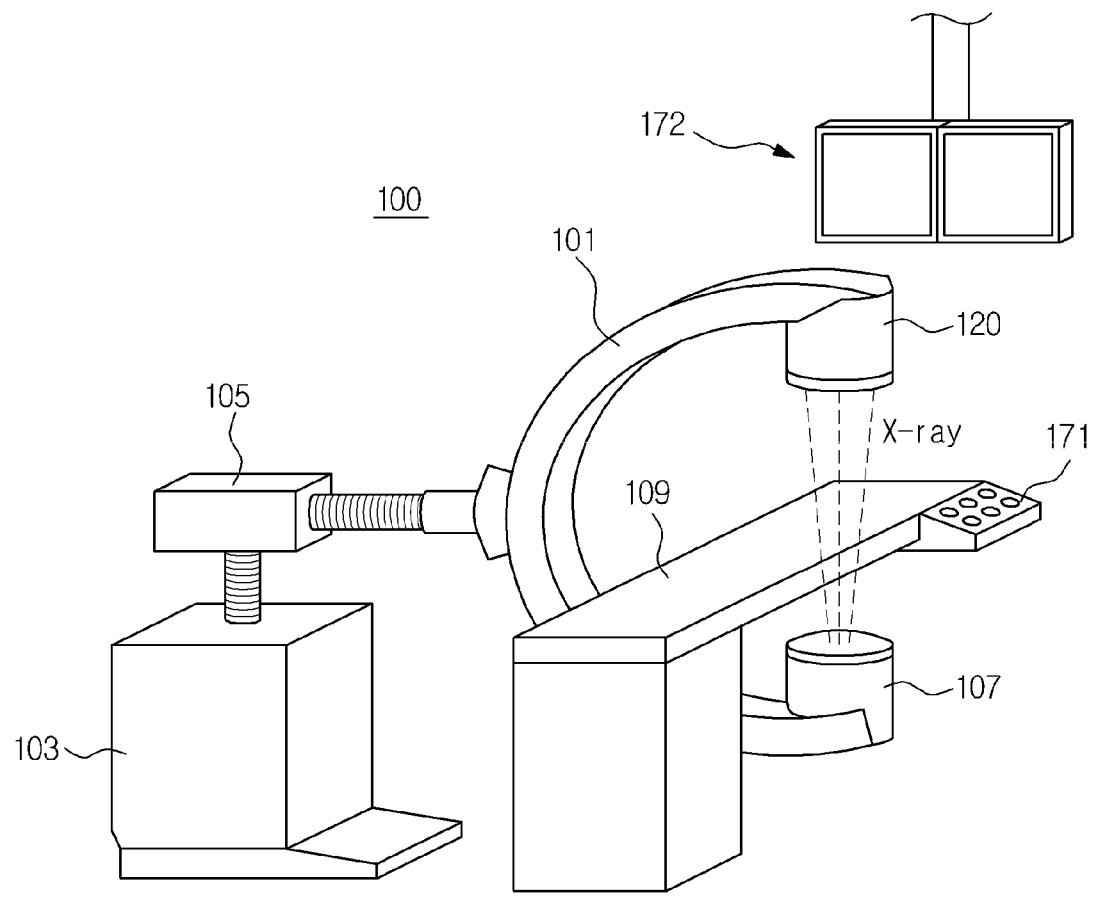
FIG. 16 is a diagram illustrating an appearance of the X-ray imaging apparatus according to an exemplary embodiment.

FIG. 16 is a diagram illustrating an appearance of the X-ray imaging apparatus according to an exemplary embodiment;

The X-ray imaging apparatus 100 may have a C-arm structure as illustrated in FIG. 16. An X-ray source assembly 107 and the X-ray detector 120 may be provided in each end of a C-arm 101 having a C shape. The C-arm 101 is connected to a main body 103 through a connecting shaft 105 and is rotatable in an orbital direction.

The inside of the X-ray source assembly 107 may include the X-ray source 110, the collimator 131, and the filtering unit 140. A patient table 109 is provided between the X-ray source assembly 107 and the X-ray detector 120. When the subject is positioned on the patient table 109, the X-ray source 110 radiates X-rays onto the subject. The X-ray detector 120 detects the radiated X-rays, and the X-ray image of the subject is obtained.

As described above, the X-ray imaging apparatus 100 may obtain a video of the subject in real time. The user may perform operations or diagnosis while watching a display 172. The display 172 can include a plurality of screens and can display several images necessary for performing operations or giving a diagnosis.

As described above, when the image analyzer 151 obtains information on the ROI or the imaging controller 162 sets the imaging parameter, information input by the user may be used. The user may input necessary information through an inputter 171 provided in the X-ray imaging apparatus 100.

Hereinafter, an exemplary embodiment of a method of controlling an X-ray imaging apparatus will be described.

Figure 17:
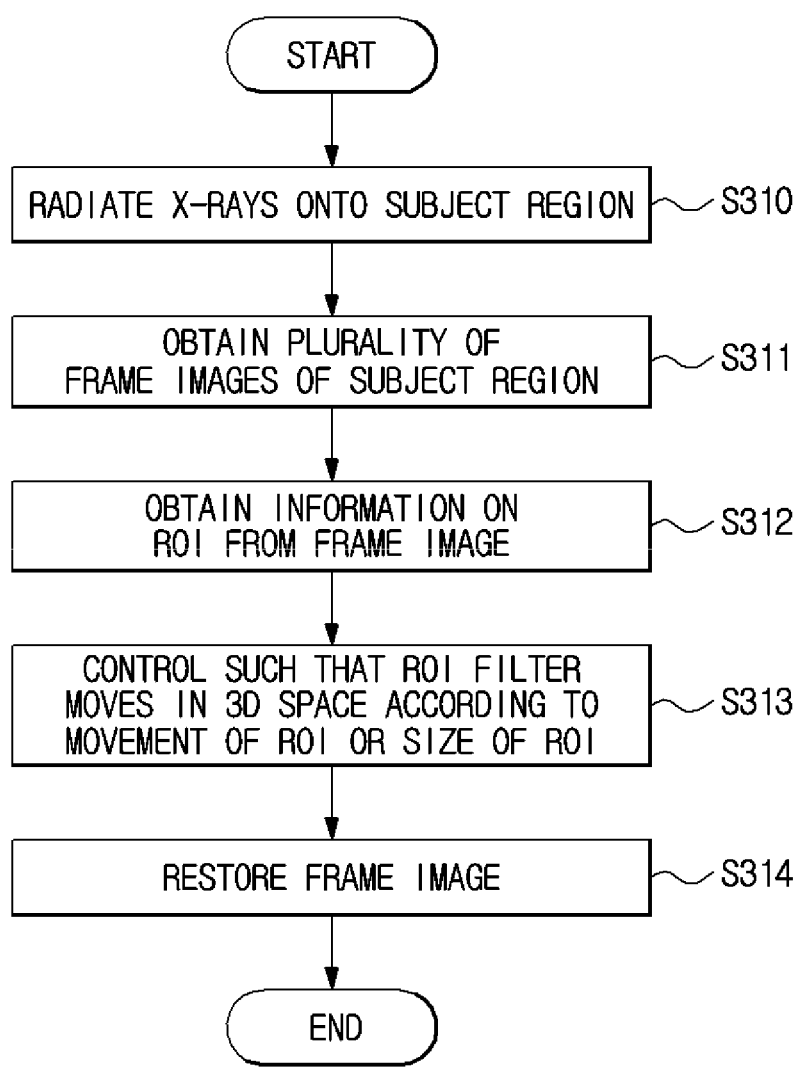
FIG. 17 is a flowchart illustrating a method of controlling an X-ray imaging apparatus according to an exemplary embodiment.

FIG. 17 is a flowchart illustrating a method of controlling an X-ray imaging apparatus according to an exemplary embodiment. The above described X-ray imaging apparatus 100 may be used in the control method.

As illustrated in FIG. 17, X-rays are radiated onto the subject region (S310). X-rays can be continuously radiated. However, in order to reduce the X-ray dose and improve temporal resolution, the pulse exposure method in which X-rays are radiated at predetermined time intervals may be applied or the continuous exposure method may be employed.

A plurality of frame images of the subject region may be obtained by detecting the radiated X-rays (S311). Obtaining the frame image may be synchronized with radiation of the X-rays and may be performed in real time.

Information on the ROI is obtained from the frame image of the subject region (S312). Obtaining the information on the ROI may include detection of the object of interest and setting of the ROI based on the detected object of interest. Specifically, the object of interest is detected from the frame image of the subject region and a specific region including the detected object of interest is set as the ROI. The information on the ROI includes the position, the size or the movement characteristic of the ROI, and the movement characteristic of the ROI may include information on the movement of the ROI.

Then, X-rays having a dose lower than that of the ROI are incident on the non-ROI. For this purpose, it is controlled such that the ROI filter moves in a 3D space according to movement of the ROI or the size of the ROI (S313). Specifically, when the ROI moves, the ROI filter 141 moves to the position corresponding to the ROI or non-ROI on the x-y plane, the changing position of the ROI or the non-ROI and the position of the ROI filter 141 may be synchronized. Also, in order to correspond the incident area of X-rays that are not filtered by the ROI filter 141 with the size of the ROI, the ROI filter 141 may move along the z-axis.

When the ROI filter 141 moves to the position corresponding to the ROI or the non-ROI and low dose X-rays are incident on the non-ROI, the frame image obtained while low dose X-rays are incident on the non-ROI is restored (S314). Specifically, it is possible to improve image quality of the non-ROI by restoring a current frame image using at least one previous frame image. The current frame image may be combined with at least one previous frame image. Examples of a method of combining the current frame image and the previous frame image include a method of averaging or summing the current frame image and the previous frame image, a method of changing a filter to be applied to the current frame image in consideration of image characteristics represented in the previous frame image such as noise and an edge direction, a method of applying motion-compensated temporal filtering, and a method of applying motion-compensated spatial filtering. Here, a combination between images may be performed on the non-ROI.

Also, additional image enforcement may be performed on the restored frame image. For example, in order to reduce degradation of resolution and image blurring that can be generated when the current frame image and the previous frame image are combined, it is possible to perform alignment or registration between frame images, or motion prediction and compensation.

Meanwhile, restoration work for improving image quality of the image may also be performed on the ROI of the frame image, and the ROI of the frame image may be restored using a de-noising algorithm such as a spatial filter, a temporal filter, a spatio-temporal filter, and super-resolution reconstruction. The ROI of the frame image may be enhanced using a detail enhancement algorithm such as a contrast enhancement algorithm based on a histogram or a wavelet, and an edge enhancement filter.

Also, an image equalization algorithm for matching brightness and contrast of the ROI and the non-ROI of the frame image is performed, and the restored frame image may be displayed in the display in real time.

The ROI filter 141 used in the method of controlling the X-ray imaging apparatus may include the plurality of filter layers as described in FIG. 9. Hereinafter, an exemplary embodiment of a method of controlling an X-ray imaging apparatus in which a plurality of filter layers are appropriately combined based on image characteristics represented in a frame image will be described.

FIG. 18 is a flowchart illustrating an exemplary embodiment of selecting a plurality of filter layers in the method of controlling an X-ray imaging apparatus. The ROI filter used in this exemplary embodiment has a plurality of filter layers, and any one, both, or neither of the thickness and the filtration material may be the same in the plurality of filter layers.

As illustrated in FIG. 18, X-rays are radiated onto the subject region (S320), and a plurality of frame images of the subject region are obtained by detecting the radiated X-rays (S321). Information on the ROI is obtained from the obtained frame image (S322). Here, the information on the ROI may further include image characteristics represented in the ROI or non-ROI of the frame image.

Based on image characteristics represented in the ROI or non-ROI of the frame image out of the information on the ROI, a filter layer to be used for filtering is selected (S323).

Then, it is controlled such that an unselected filter layer is outside the filtering position (S324), and the selected filter layer moves to the filtering position (S325). In order to move the filter layer to the outside of the filtering position, a corresponding filter layer moves along the z-axis as described in FIGS. 11A to 11D, a corresponding filter layer moves on the x-y plane as described in FIGS. 12A to 12D, and a corresponding filter layer is divided into two or more pieces and the divided pieces move further from X-rays on the x-y plane as described in FIGS. 13A and 13B.

According to the X-ray imaging apparatus and the method of controlling the same described above, X-rays having a dose lower than that of the ROI are incident on the non-ROI using the ROI filter, thereby implementing low dose X-ray imaging and minimizing FOV loss of the X-ray image. In addition, movement of the ROI and movement of the ROI filter are synchronized, thereby it applying in the field of the X-ray video. Also, the ROI filter is automatically movable according to a position change of the ROI, thereby securing continuity of operation procedures using the X-ray imaging apparatus.

X-rays having a dose lower than that of the ROI are incident on the non-ROI using the ROI filter, thereby implementing low dose X-ray imaging and minimizing FOV loss of the X-ray image.

Also, by synchronizing movement of the ROI with movement of the ROI filter, it can be applied to the field of the X-ray video.

Therefore, by using an ROI filter as disclosed in the exemplary embodiments, the size and position of the ROI filter can be dynamically controlled and the amount of X-ray attenuation can be controlled. Further, the ROI filter as disclosed in the exemplary embodiments can be dynamically moved three-dimensionally.

Although the exemplary embodiments have been shown and described, it would be appreciated by those skilled in the art that changes may be made in these exemplary embodiments without departing from the principles and spirit of an exemplary embodiment, the scope of which is defined in the claims and their equivalents.

What is claimed is:

1. An X-ray imaging apparatus, comprising:
an X-ray source configured to radiate X-rays onto a subject region;
an X-ray detector configured to detect the radiated X-rays, and obtain a plurality of frame images of the subject region, based on the detected X-rays;
a collimator disposed between the X-ray source and the X-ray detector, and configured to adjust a range of the subject region; and
a region of interest (ROI) filter disposed between the collimator and the X-ray detector, and configured to filter the X-rays radiated from the X-ray source, the ROI filter comprising a plurality of filter layers,
wherein a first filter layer among the plurality of filter layers is configured to be disposed above a second filter layer among the plurality of filter layers and along a line orthogonal to surfaces respectively of the collimator and the X-ray detector, the surfaces face each other, and each of the plurality of filter layers is configured to be independently translatable in a direction along the line toward the collimator or the X-ray detector.

2. The apparatus according to claim 1, wherein the ROI filter is further configured to filter the X-rays radiated from the X-ray source so that X-rays having a dose lower than a dose of an ROI are incident on a non-ROI inside of the subject region.

3. The apparatus according to claim 2, further comprising a controller configured to control the ROI filter to move in a three-dimensional space that is defined by an x-axis, a y-axis, and a z-axis, based on a movement of the ROI or a size of the ROI.

4. The apparatus according to claim 3, further comprising an image processor configured to obtain information of the ROI from at least one frame image among the plurality of frame images, and transmit the obtained information to the controller.

5. The apparatus according to claim 4, wherein the information of the ROI comprises any one or any combination of a position, the size, and a movement characteristic of the ROI, and image characteristics of the ROI and the non-ROI of the at least one frame image.

6. The apparatus according to claim 5, wherein the image processor is further configured to detect an object of interest from the at least one frame image, and set the ROI, based on any one or any combination of a position, a size, and a movement characteristic of the object of interest.

7. The apparatus according to claim 6, wherein the image processor is further configured to set the ROI in real time, and obtain the ROI at a predetermined frame rate.

8. The apparatus according to claim 3, wherein the controller is further configured to control the ROI filter to move toward one of the collimator and the X-ray detector to a position corresponding to the size of the ROI along the z-axis, and move to a position corresponding to a position of the ROI on an x-y plane that is defined by the x-axis and the y-axis.

9. The apparatus according to claim 8, wherein the ROI filter comprises:
a filtration material configured to reduce a number of the X-rays incident on the non-ROI; and
an opening configured to allow the X-rays incident on the ROI to pass through.

10. The apparatus according to claim 9, wherein the position corresponding to the size of the ROI is a position in which an incident region of X-rays passing through the opening matches the ROI.

11. The apparatus according to claim 7, wherein the controller is further configured to control the ROI filter to move in real time, based on the ROI that is set in real time, the ROI filter being moved separately from the X-ray source and the X-ray detector.

12. The apparatus according to claim 5, wherein the controller is further configured to independently control movement of each of the plurality of filter layers.

13. The apparatus according to claim 12, wherein the controller is further configured to determine a difference between X-ray doses to be incident on the ROI and the non-ROI, based on the image characteristics of the ROI and the non-ROI of the at least one frame image.

14. The apparatus according to claim 13, wherein the controller is further configured to select at least one filter layer among the plurality of filter layers, based on the determined difference, and control the selected at least one filter layer to be positioned at a filtering position to filter the radiated X-rays.

15. The apparatus according to claim 14, wherein the controller is further configured to control an unselected filter layer among the plurality of filter layers to move along the z-axis and on an x-y plane that is defined by the x-axis and the y-axis to a position outside of the filtering position.

16. The apparatus according to claim 12, wherein each of the plurality of filter layers comprises any one or any combination of a different kind and a different thickness of a filtration material.

17. A method of controlling an X-ray imaging apparatus, the method comprising:
controlling an X-ray source to radiate X-rays onto a subject region;
adjusting a range of the subject region, using a collimator;
detecting, by an X-ray detector, the radiated X-rays;
obtaining information of a region of interest (ROI) inside of the subject region, based on the detected X-rays; and
controlling an ROI filter configured to filter X-rays incident on a non-ROI inside of the subject region, based on a movement of the ROI or a size of the ROI, the ROI filter being disposed between the collimator and the X-ray detector, and the ROI filter comprising a plurality of filter layers,
wherein a first filter layer among the plurality of filter layers is disposable above a second filter layer among the plurality of filter layers and along a line orthogonal to surfaces respectively of the collimator and the X-ray detector, the surfaces face each other, and each of the plurality of filter layers is independently translatable in a direction along the line toward the collimator or the X-ray detector.

18. The method according to claim 17, wherein the controlling the ROI filter to move comprises controlling the ROI filter to move in a three-dimensional space that is defined by an x-axis, a y-axis, and a z-axis, based on the movement of the ROI or the size of the ROI.

19. The method according to claim 18, wherein the obtained information of the ROI comprises any one or any combination of a position, the size, and a movement characteristic of the ROI, and image characteristics of the ROI and the non-ROI.

20. The method according to claim 18, wherein the controlling the ROI filter to move comprises controlling the ROI filter to move toward the X-ray source and the X-ray detector to a position corresponding to the size of the ROI along the z-axis, or move in real time to a position corresponding to a position of the ROI on an x-y plane that is defined by the x-axis and the y-axis, based on the information of the ROI obtained in real time.

* * * * *